United States Patent
Figulla et al.

(10) Patent No.: US 7,955,354 B2
(45) Date of Patent: Jun. 7, 2011

(54) OCCLUSION DEVICE AND SURGICAL INSTRUMENT AND METHOD FOR ITS IMPLANTATION/EXPLANTATION

(75) Inventors: Hans Reiner Figulla, Jena (DE); Friedrich Moszner, Hohlstedt (DE); Robert Moszner, Bad Klosterausnitz (DE); Rüdiger Ottma, Grossschwabhausen (DE)

(73) Assignee: Occlutech GmbH, Jena (DE)

( * ) Notice: Subject to any disclaimer, the term of this patent is extended or adjusted under 35 U.S.C. 154(b) by 85 days.

(21) Appl. No.: 11/271,752

(22) Filed: Nov. 14, 2005

(65) Prior Publication Data

US 2007/0112381 A1    May 17, 2007

(51) Int. Cl.
*A61B 17/08* (2006.01)
(52) U.S. Cl. .................................................. 606/213
(58) Field of Classification Search .................. 606/113, 606/139, 142, 200, 205, 213, 215, 108, 191–199; 623/1.11, 1.23; 403/11, 19, 119, 122, 124, 403/143; 604/19
See application file for complete search history.

(56) References Cited

U.S. PATENT DOCUMENTS

| | | | |
|---|---|---|---|
| 5,108,420 A | | 4/1992 | Marks |
| 5,201,741 A | | 4/1993 | Dulebohn |
| 5,217,484 A | * | 6/1993 | Marks ........................ 606/200 |
| 5,433,727 A | * | 7/1995 | Sideris ........................ 606/213 |
| 5,725,552 A | * | 3/1998 | Kotula et al. .................. 606/213 |
| 6,174,322 B1 | * | 1/2001 | Schneidt ........................ 606/213 |
| 6,277,125 B1 | * | 8/2001 | Barry et al. .................... 606/108 |
| 6,849,081 B2 | * | 2/2005 | Sepetka et al. ................ 606/213 |
| 7,169,167 B2 | * | 1/2007 | Chu ............................... 606/205 |
| 7,431,729 B2 | * | 10/2008 | Chanduszko ................ 606/213 |
| 2002/0013592 A1 | * | 1/2002 | Osypka ........................ 606/158 |
| 2004/0143293 A1 | | 7/2004 | Marino et al. |

FOREIGN PATENT DOCUMENTS

| | | |
|---|---|---|
| DE | 690 01 759 T2 | 1/1994 |
| DE | 195 47 617 C1 | 9/1997 |
| DE | 100 00 137 A1 | 7/2001 |
| DE | 100 35 230 A1 | 2/2002 |
| DE | 103 38 702 B3 | 3/2005 |
| EP | 0 698 373 A2 | 2/1996 |
| WO | WO 94/06502 A | 3/1994 |
| WO | WO 01/58381 A1 | 8/2001 |
| WO | WO 03/077776 A | 9/2003 |
| WO | WO 2005/037140 A1 | 4/2005 |

* cited by examiner

*Primary Examiner* — Todd E Manahan
*Assistant Examiner* — Lindsey Bachman
(74) *Attorney, Agent, or Firm* — Inskeep IP Group, Inc.

(57) ABSTRACT

An occlusion device includes a braiding of thin wires or threads tapering to the diameter of a catheter used for an intravascular implantation/explantation procedure and having a proximal retention area, a distal retention area at which ends of the wires or threads converge into a holder, and a cylindrical crosspiece interposed between the proximal retention area and the distal retention area, whereby the two retention areas are positioned on two sides of a shunt to be occluded in a septum following implantation while the crosspiece transverses the shunt. The holder exhibits a head section at its free end having an eyelet as a cross-hole which can be gripped and held in form-fit fashion by an implantation/explantation instrument. A surgical instrument having such a holder includes gripper tongs with gripping jaws which open and close by a push/pull system, and which force-fit grips the head section of the holder.

1 Claim, 18 Drawing Sheets

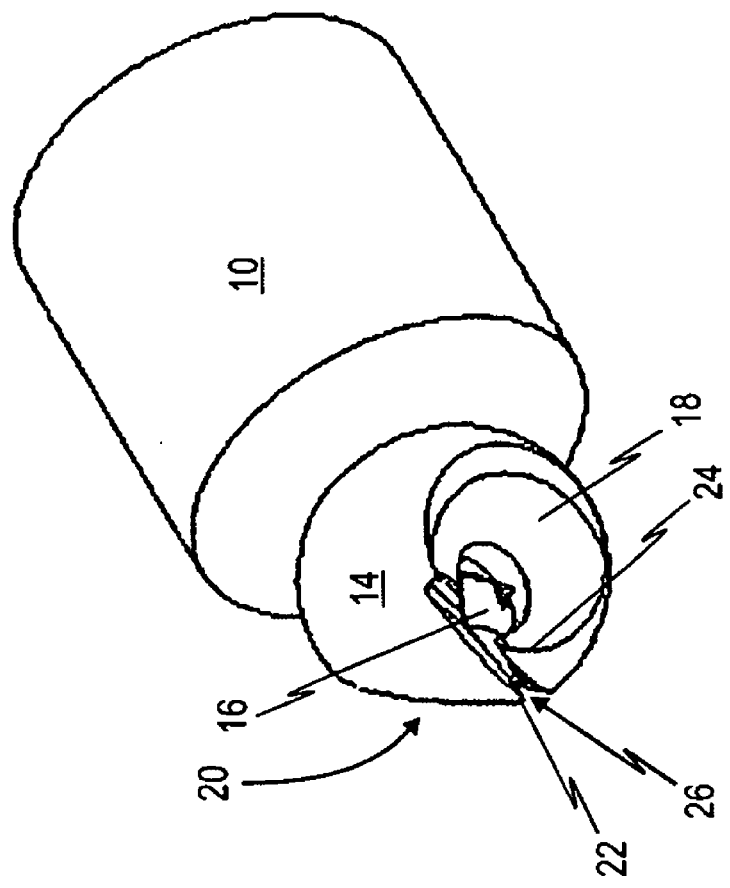
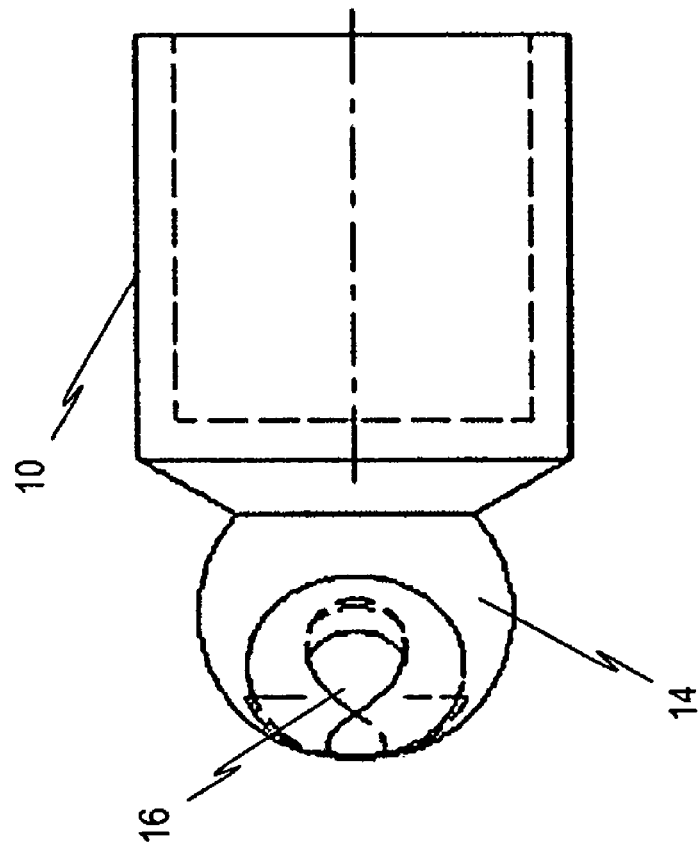
Fig. 11
Fig. 10

OCCLUSION DEVICE AND SURGICAL INSTRUMENT AND METHOD FOR ITS IMPLANTATION/EXPLANTATION

The present invention relates to an occlusion device and a surgical instrument for the implantation/explantation of an implant.

BACKGROUND OF THE INVENTION

1. Field of the Invention

The present invention relates to an occlusion device consisting of a braiding of thin wires given a suitable form by means of a molding and heat treatment procedure and which tapers to the diameter of a catheter used for an intravascular implantation or explantation procedure having a proximal retention area, a distal retention area, at which the ends of the wires or threads converge into a holder, and having a cylindrical crosspiece interposed between said proximal retention area and said distal retention area, whereby the two retention areas position on the two sides of a shunt to be occluded in a septum following implantation while the crosspiece transverses the shunt. The invention moreover relates to a surgical instrument for the implantation and explantation of an implant, in particular an occlusion device as described above. Lastly, the present invention relates to a method for the repeated coupling of an implant, in particular an occlusion device as described above, to such a surgical instrument.

2. Description of the Related Art

Medical technology has long endeavored to be able to occlude septal defects, for instance atrioseptal defects, by means of non-surgical transvenous catheter procedures, in other words, without having to perform an operation in the literal sense. Various different occlusion systems have been proposed to this end, each with their own pros and cons, without any one specific occlusion system having yet become widely accepted. In making reference to these different systems, the following will use the terms "occluder" or "occlusion device." In all interventional occlusion systems, a self-expanding umbrella system is introduced transvenously into a defect to be occluded in a septum. This type of system might comprise two umbrellas; one positioned, for example, at the distal side of the septum (i.e., the side furthest from the median plane of the body/heart) and one at the proximal side of the septum (i.e., the side closer to the median plane of the body), whereby the two umbrella prostheses are subsequently secured to a double umbrella in the septal defect. Thus, in the assembled state, the occlusion system usually consists of two clamped umbrellas connected to one another by means of a short bolt transversing the defect. However, a disadvantage to such prior art occlusion devices turns out to be the relatively complicated, difficult and complex implantation procedure. Apart from the complicated implantation of the occlusion system in the septal defect to be occluded, the umbrellas utilized are susceptible to material fatigue along with fragment fracture. Furthermore, thromboembolic complications are frequently to be anticipated.

In order to enable the inventive occlusion device to be introduced by means of a surgical insertion instrument and/or guidewire, a holder is provided at the end of the distal retention area which can engage with the insertion instrument and/or guidewire. It is thereby provided for this engagement to be readily disengaged after positioning the occlusion device in the defect. For example, it is possible to devise the braiding at the end of the distal retention area of the occlusion device in such a manner so as to create an internal threading in the holder to engage with the insertion instrument.

In previously-known occluders made of a nitinol wire braiding, for example from AGA or JEN.meditec, the coupling to the insertion wire is configured as a screw threading. The insertion wire provides for the occluder to be urged forward or backward within the catheter tube. After the occluder has been positioned in the septum of the heart, the insertion wire is unscrewed and the occluder ultimately released. No corrections are thereafter possible.

Since the insertion wire and the coupling are relatively rigid and the catheter approaches the septum of the heart at a shallow angle in the minimally invasive implantation of the occluder through the leg artery for anatomical reasons, the occluder remains tilted upon its unfolding and the umbrellas cannot abut both sides of the shunt. In a situation such as this, the operating surgeon cannot discern whether the occluder will assume its predetermined fit once uncoupled. This gives rise to great uncertainty for the surgeon, in particular since his only means of repositioning an uncoupled occluder is a non-minimally invasive procedure.

The present invention is based on minimizing these crucial disadvantages of the known systems, namely by allowing the occluder all freedom of movement for its independent unfolding and adapting to the septal defect to be occluded after its having been positioned in the septum of the heart and released from the insertion port, and not having it be forced into a position by the insertion instrument which it would not automatically assume by itself and yet having it be repositionable and retrievable with a insertion instrument as necessary.

Of course, other embodiments are also conceivable here as well. With another type of occlusion device, the so-called Lock-Clamshell umbrella system, two stainless steel preferably Dacron-covered umbrellas are provided, each stabilized by four arms. This type of occluder is implanted into the patient through a vein. However, seen as problematic with the Lock-Clamshell occluder is the fact that the insertion instruments necessary to implant the device need to be of relatively large size. A further disadvantage seen with other systems, e.g. the so-called "Amplatz occluder," is that many different occluder sizes are needed in order to cope with the respective dimensions of the septal defects to be occluded. It thus turns out that the umbrellas do not flatten out completely in the inserted state if the length or the diameter of the crosspiece inserted into the defect is not of an optimum fit. This results in incomplete endothelialization. It has furthermore been shown that many of the systems implanted into patients' bodies exhibit material fatigue and fractures in the metallic structures due to the substantial mechanical stresses over a longer period. This is especially the case given permanent stress between an implant and the septum.

In order to overcome these disadvantages, self-centering occlusion devices have been developed which are inserted into the body of the patient and introduced into the septal defect to be occluded by way of a minimally invasive procedure, for example using a catheter and guidewires. Their design is based on the principle that the occlusion device can be tapered to the dimensions of the insertion instrument and/or catheter used for the intravascular procedure. Such a tapered occlusion device is then introduced by catheter into the septal defect to be occluded, respectively into the shunt of the septal defect to be occluded. The occluder is then discharged from the catheter, upon which the self-expanding umbrellas, retention plates respectively, subsequently unfold against the two sides of the septum. The umbrellas in turn comprise fabric inserts made from or covered by, for example, Dacron, with which the defect/shunt is occluded. The implants remaining in the body are more or less completely ingrown by the body's own tissue after a few weeks or months.

An example of a self-centering occlusion device of the type specified at the outset and in accordance with the prior art is known from WO 99/12478 A1, which is a further development of the occlusion device known as the "Amplatz occluder" in accordance with U.S. Pat. No. 5,725,552. Same consists of a braiding of a plurality of fine, intertwined nitinol wire strands in the shape of a yo-yo. Each braiding is produced in its original form as a rounded braiding having loose wire ends both at its leading end (its proximal side, respectively) as well as at its trailing end (its distal side, respectively). During the subsequent processing of the rounded braiding, each of these loose ends must then be gathered into a sleeve and welded together. After such appropriate processing, both the proximal side as well as the distal side of the finished occluder exhibit a protruding collar. Dacron patches are sewn into the distal and proximal retention umbrellas and the interposed crosspiece. Because of the "memory effect" exhibited by the nitinol material used, the two retention umbrellas unfold by themselves upon exiting the catheter, initially in a balloon-like intermediate stage, whereby the retention umbrellas ultimately positioned on the two sides of the septum eventually assume a more or less flattened form. The crosspiece centers itself automatically into the shunt to be occluded as the umbrellas unfold. Because the collar protrudes past the proximal retention area of the occluder, the problem can arise that the inserted implant causes embolic-related problems, in particular consecutive embolization. Furthermore, a complete endothelialization of occluder implant is often hindered.

An occlusion device made of wire braiding is furthermore known from WO 95/27448 A1. This device, however, does not have a holder such that this occluder cannot be guided during introduction by an insertion instrument in the same way as is the case with the devices described above, nor can it be—in the case of a poor seating—retracted again prior to being uncoupled.

The problem therefore set out for the present invention is to refine such a braided self-centering occlusion device as known to medical technology such that the disadvantages cited above will be overcome. A particular objective is the providing of an occlusion device applicable to occluding defects of different sizes, whereby implantation of the occluder is to be a simple matter and with which explantation is also possible; e.g. to correct improper seating.

SUMMARY OF THE INVENTION

Based on the problem as posed, it is the task of the present invention to provide an occlusion device which, in the inserted state at the proximal end of the septal defect, lies as flat as possible against the septum and which can be retrieved following uncoupling should improper positioning be indicated.

A further task of the present invention is providing the corresponding surgical instrument as well as a method for the repeatable coupling of an occlusion device to such a surgical instrument.

These tasks are solved with the inventive occlusion device of the type specified at the outset by the provision of a holder having a head section at its free end comprising an eyelet in the form of a cross-hole which can be force-fit to and held by an implantation or explantation instrument. Alternatively hereto, the task is inventively solved with an occlusion device of the type specified at the outset by the provision of a holder having a head section at its free end configured as a semi-spherical centering sleeve in longitudinal section comprising an eyelet in the form of a cross-hole able to be held to an implantation/explantation instrument by means of running a fastening loop through it.

The procedural task set forth for the present invention is alternatively solved by a method for the repeatable coupling of an implant having a holder, in particular an occlusion device, to a surgical instrument, wherein a loop of insertion thread or guidewire is guided through the eyelet of the holder of the implant prior to beginning the intravascular procedure and hooked on a fix point provided for the purpose on gripper tongs while the first and second loose ends of the insertion thread or guidewire are held or fastened in the area of the first gripping sections, where the head section of the holder of the implant is grabbed by gripping tongs; the second loose end of the insertion thread/guidewire provided with a nipple is tightened until the head section is fully accommodated within the gripping jaws; then releasing the second loose end provided with the nipple releases gripper tongs from the head section of the implant and the seating of the implant is checked; and where the insertion thread/guidewire allows the gripper tongs to recouple with the holder of the implant at any time.

In addition, the method for the repeatable coupling of an implant having a holder, in particular an occlusion device, to a surgical instrument, includes the loop of insertion thread or guidewire being guided through the diagonal slot in the eyelet of the holder of the implant prior to beginning the intravascular procedure while the first and second loose ends of the insertion thread or guidewire are held or fastened in an area of said first gripping section; where head section of the holder of the implant is grabbed by gripping tongs; where the second loose end of the insertion thread or guidewire provided with a nipple is tightened until the head section is accommodated within gripping jaws; where releasing the second loose end provided with the nipple prompts the releasing of gripping tongs from head section of the implant and the seating of the implant is checked; where insertion thread/guidewire allows gripper tongs to recouple with the holder of the implant at any time.

Finally, a method for the repeatable coupling of an implant having a holder, in particular an occlusion device, to a surgical instrument includes a fastening loop of defined length being fastened to eyelet of the holder of the implant; said fastening loop being then inserted into the cross-groove of the cylindrical sleeve such that the knot of the fastening loop fits centrically through the protrusion and the section of fastening loop positioning in cross-groove is held diametrically; where upon a defined forward shifting of the hook, the section of the fastening loop in the cross-groove slips over the hook in the second longitudinal groove and remains anchored there; where withdrawing of said hook pulls and clamps the holder of the implant to the proximal face side of sleeve; where a renewed defined forward displacing of hook will again loosen fastening loop and the proximal front side of sleeve loosens from holder and the seating of the implant can be checked; where the use of the fastening loop allows recoupling of sleeve to the holder of the implant at any time.

Hence disclosed here as a solution to the task facing the present invention is an entire system comprising an implant in the form of an occlusion device, an applicable surgical instrument thereto and a corresponding method for the use of said surgical instrument.

Inventive advantages are in particular seen in the provision of an intravascular occlusion device, especially for the treatment of septum defects, which affords a reliable hold during the implantation operation with a correspondingly configured surgical instrument and which can be released from the surgical instrument for the purpose of verifying how the occlusion device is seated, whereby particularly emphasized is the fact that it is readily possible to subsequently take hold of the occlusion device again, for example in order to change its positioning or to effect immediate explantation.

Three alternative embodiments are herewith proposed for configuring the holder of the occlusion device in accordance with the invention.

Firstly, the head section of the holder can be configured as a spherical head whereby the inside of the jaws of the surgical instrument's gripper tongs, which correspond to the shape of the spherical head, are configured so as to ensure a form-fit gripping of said spherical head by the surgical instrument's gripper tongs. So that a subsequent renewed gripping of the spherical head will be readily possible after the connection between the surgical instrument and the occlusion device has been disengaged, the surgical instrument exhibits an insertion thread or guidewire which protrudes in the form of a loop from the proximal end of the surgical instrument's gripper tongs in its delivery state, its two loose ends being held or having been previously affixed near the grip for the surgeon on the surgical instrument. Said insertion thread or guidewire allows the gripper tongs of the surgical instrument to easily and precisely reconnect to the head section of the occlusion device's holder and thus re-grip the occlusion device—for the purpose of repositioning or explantation, for example.

In accordance with a second embodiment of the occlusion device holder, the eyelet of the head section is slit diagonally to the cross-hole whereby the ends of the diagonal slot overlap with respect to the longitudinal direction of the cross-hole. This thus enables the insertion thread/guidewire, which protrudes from the gripper tongs in the form of a loop at the proximal end of the surgical instrument in delivery state, to hook into the diagonal slot in the eyelet of the occlusion device holder whereby the overlapping ends of the diagonal slot ensure that the insertion thread/guidewire cannot readily, and in particular not after said insertion thread/guidewire is tensioned by the surgeon, inadvertently break free of the eyelet and yet can nevertheless be intentionally moved out of the eyelet through the diagonal bearing of the loop.

The dual-sided cut discharge surface of the cross-hole is preferably configured to converge with the outer surface of the spherical head toward the free end of the holder. This has the advantage of there being no sharp edges which could damage the insertion thread or guidewire and in addition facilitates threading the loop of the insertion thread/guidewire through the eyelet of the holder of the first embodiment. Last but not least, the converging configuration to the cut discharge surface of the cross-hole entails less material and weight.

In accordance with a third embodiment of the occlusion device holder, the head section is formed as a semi-spherical centering sleeve in longitudinal section and likewise provided with an eyelet in the form of a cross-hole. To connect with the corresponding surgical instrument, a fastening loop, made of surgical suture for example, is fed through the eyelet and, keeping to a defined width of the fastening loop, its two ends are knotted and hooked to the hooks of the corresponding surgical instrument. While with the first and the second embodiment of the holder's head section, the tensioning of the insertion thread or guidewire ensues manually by the surgeon pulling on one or both loose ends of said insertion thread or guidewire, in the third embodiment, the tensioning of the fastening loop ensues through the retraction of the hook within the surgical instrument.

In the first and second embodiments, the push-pull system of the surgical instrument preferably comprises the following components: a coil spring, an actuator means extending axially through its interior which is sufficiently rigid in the axial direction yet still flexible and having a shaft of the gripper tongs attached to its proximal end as well as a first gripping section at its distal end. The push-pull system moreover comprises a taper sleeve for receiving the shaft of the axially-displaceable gripper tongs at its proximal end section and the proximal end of the coil spring is received by abutting against a stop at its distal end section. A second gripping section is also included here at which the distal end of the coil spring is received by abutting against a stop whereby the gripping jaws close from the force exerted by the coil spring on the outer adjacent proximal frontal end of the taper sleeve and open as a result of the forward advancing of the actuator means. The advantage of this push-pull system essentially lies in its simplicity, and the therein associated reliability of its components, and in the secure gripping and releasing of the implant's holder.

In the first embodiment of the holder, the loop of the insertion thread or guidewire, protruding as such from the gripping tongs in the delivery state of the surgical instrument at its proximal end, and which is guided through the interior of the taper sleeve and the interior of the coil spring to the first gripping section at the distal end of the surgical instrument by both loose ends, is passed through the eyelet of the implant's holder and affixed to the gripping tongs prior to implantation of the implant. Tensioning the insertion thread or guidewire leads to connecting the surgical instrument to the holder of the occlusion device, which can occur repeatedly while maintaining the connection.

Thus, the connection between the surgical instrument and the occlusion device—to the insertion thread/guidewire—can, for example, initially be disengaged in order to verify the seating of the implant, and can readily be restored using the insertion thread/guide-wire should the seating of the implant be changed and the surgical instrument thus needs to re-grip the implant's holder. Also, should it become necessary for the implant to be explanted again, a simple re-establishing of the connection between the surgical instrument and the implant is thereby enabled. In contrast, the loop in the second embodiment is hung through the diagonal slot in the eyelet and not, as is the case in the first embodiment, guided through the eyelet.

In both the first as well as the second embodiment of the holder, a first loose end of the insertion thread or guidewire can be fastened in the area of a first gripping section while the second loose end of the insertion thread or wire is provided with a nipple for either aiding in the tensioning of the insertion thread/guidewire in the coupled state of the implant or extraction from the surgical instrument after the connection of the first end is disengaged from the gripping section. In the second embodiment of the holder, the loop of the insertion thread or guidewire can thereby be moved out of the eyelet through the diagonal slot after at least one loose end of the insertion thread/guidewire has been relaxed.

The insertion thread or guidewire is preferably made from a nitinol wire, of which, for example, also the braiding of the occlusion device itself can be composed. Nitinol is a proven material in such surgical procedures.

For the third embodiment of the holder of an occlusion device, a surgical instrument is provided with a hook which can move axially along the eyelet, toward and away from same, by means of a push/pull system, whereby a fastening loop which extends through the eyelet and which can be hooked to the hook is used, by means of which the implant can be held to the surgical instrument by tensioning the fastening loop when the hook is moved away from the eyelet. The advantage to this embodiment of the surgical instrument is particularly noted to be that the insertion thread or guidewire is replaced by the fastening loop, thereby dispensing with the need to pull on the loose ends of said insertion thread or guidewire in order to tension the entire device as described with respect to the other two embodiments; the tensioning instead ensues from withdrawing the hook, which can follow from the appropriate actuating of the surgical instrument.

In the third embodiment of the surgical instrument, the push/pull system essentially comprises the following components: a coil spring, an actuator means extending axially through its interior which is sufficiently rigid in the axial direction yet still flexible and having a shaft of the hook attached at its proximal end and a first gripping section affixed to its distal end; a cylindrical sleeve which receives the proximal end of the coil spring by abutting against a stop at its the distal end section and which accommodates the shaft of the hook in axially-displaceable fashion; and a second gripping section which receives the distal end of the coil spring by abutting against a stop whereby the hook is axially displaced away from the eyelet from the force exerted by the coil spring and which is moved toward the eyelet by the forward advancing of the actuator means. This push-pull system likewise enables a very easy and reliable manipulating of the occlusion device both before and during the surgical procedure.

In order to even further simplify the connection of the fastening loop extending through the eyelet of the occlusion device holder to the push-pull system, it is preferably provided for the cylindrical sleeve to have a continuous first longitudinal groove on the proximal forward side, a second longitudinal groove at one side of its center section for the anti-twist guiding of the axially-displaceable hook in the sleeve, and a cross-groove disposed at a right angle to the second longitudinal groove on the one side which extends to the longitudinal axis of the sleeve and has a protrusion at its center for receiving a knot of the fastening loop. The protrusion to receive the knot of the fastening loop also ensures, among other things, that the fastening loop is seated firmly within the cross-groove.

In order to ensure the hook can securely grip the fastening loop, it is preferably provided for the cross-section of the forward section of the hook to be configured roughly one-third flatter than the cross-section of the shaft and to exhibit play when fitted into the second longitudinal groove of the cylindrical sleeve.

To sever the connection between the surgical instrument and the implant holder, a blade is provided at the distal end of the gap configured behind the hook.

While it is preferable for the material of the surgical instrument's actuator means to be a wire, absolutely any other material which is rigid enough in the axial direction yet still sufficiently flexible can also be used.

There has thus been outlined, rather broadly, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

The following will make reference to the drawings in providing a more precise detailing of the three preferred embodiments of the occlusion device and the three embodiments of a surgical instrument related thereto as well as the three different methods for a repeatable coupling of an implant, occlusion device respectively, to the associated surgical instrument. In conjunction hereto, embodiment 1 is represented in FIGS. 1 to 7, embodiment 2 in FIGS. 8 to 14, and embodiment 3 in FIGS. 15 to 24.

FIG. 10 shows an enlarged side view of a holder of an occlusion device in accordance with embodiment 2;

FIG. 11 shows a perspective representation of the holder pursuant to FIG. 10;

DESCRIPTION OF THE INVENTION

Figure 1:
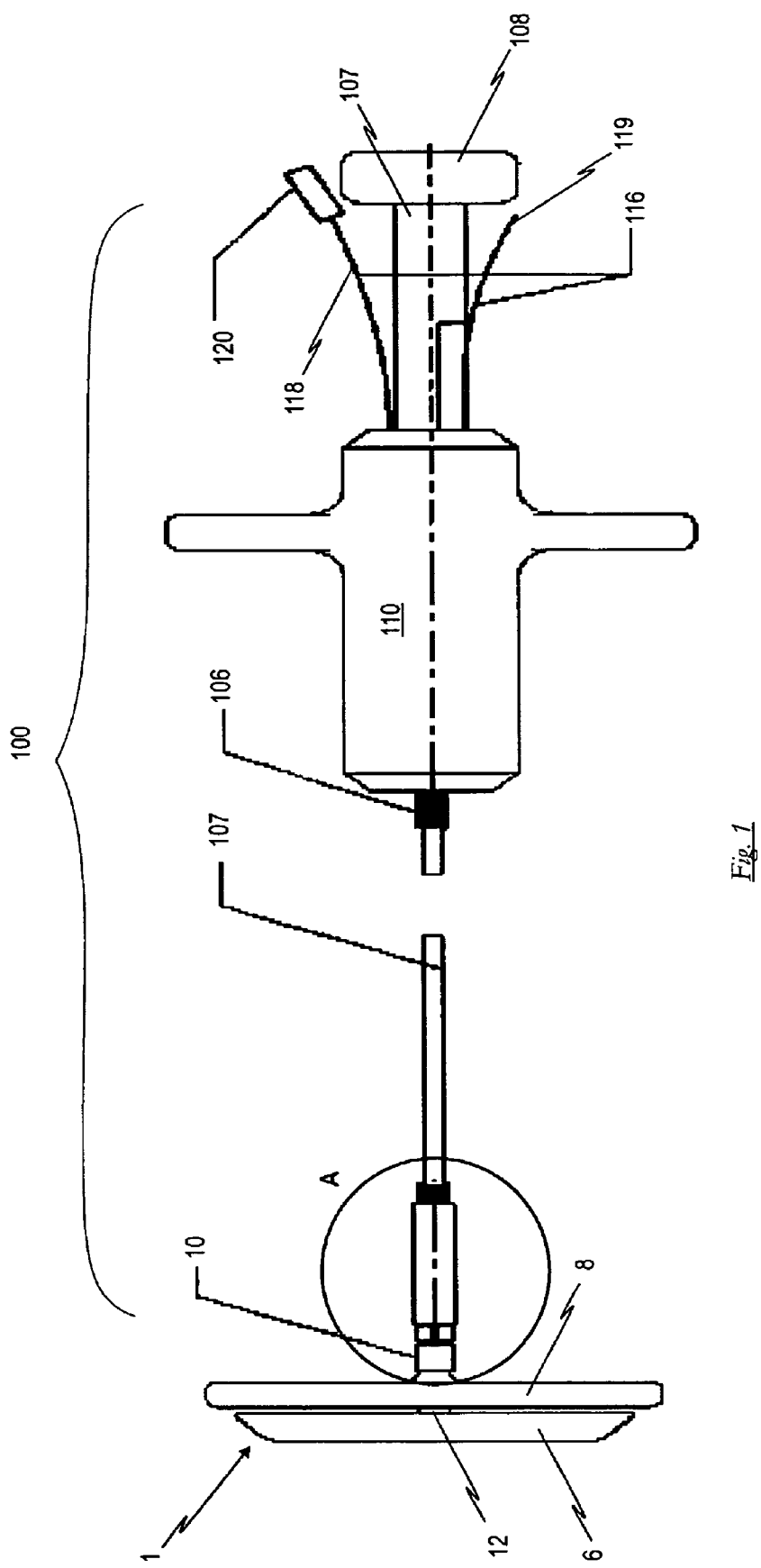
FIG. 1 shows a side view of a first embodiment of an occlusion device with a surgical instrument associated therewith in accordance with embodiment 1.
Figure 2:
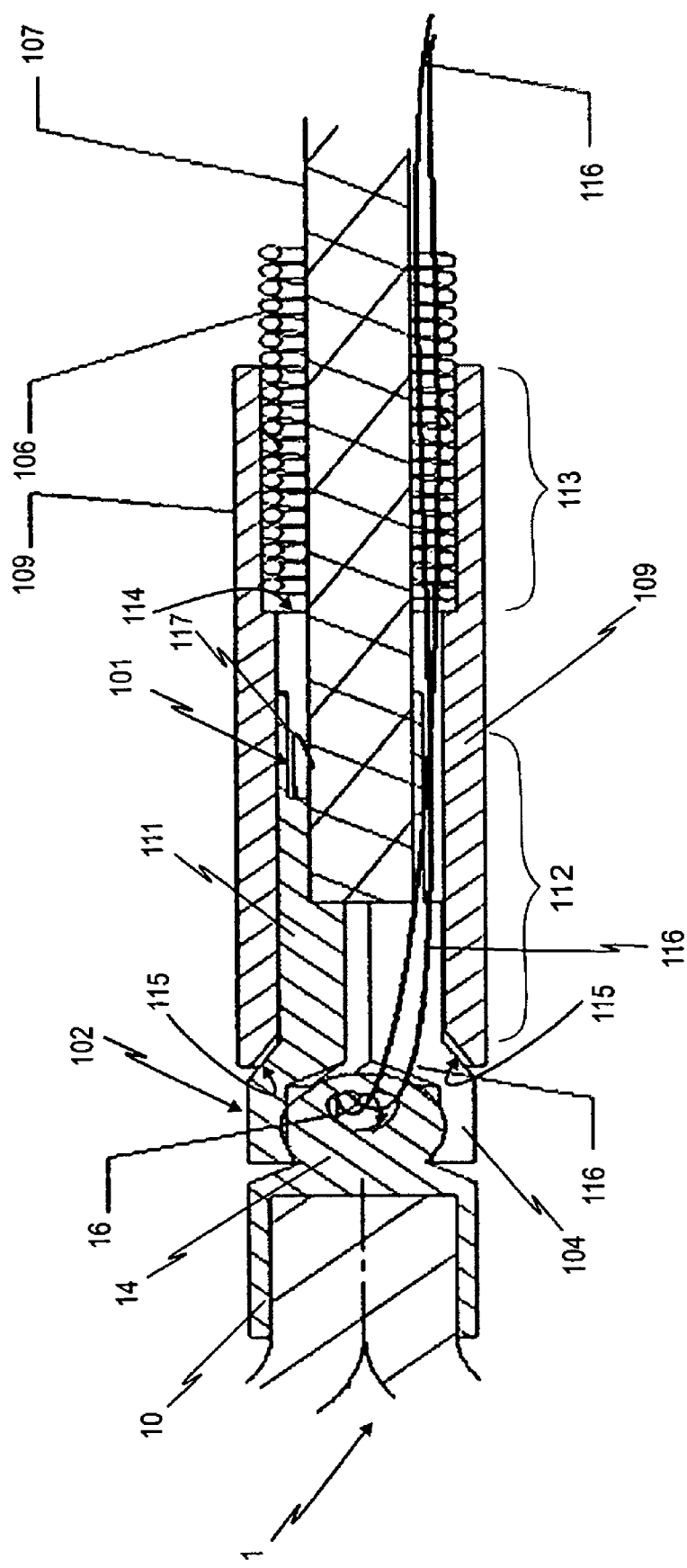
FIG. 2 shows an enlarged sectional representation of the partial "A" section pursuant to FIG. 1.

FIGS. 1 and 2 show a side and detail view of a first embodiment of a surgical instrument 100 for the implantation and explantation of an implant serving here as an example of an implant coupled to an occlusion device 1. Surgical instrument 100 exhibits gripper tongs 102, the gripping jaws 103, 104, 105 of which can be opened and closed by means of a push/pull system. The inside areas of gripping jaws 103, 104, 105 are configured such that they can grab the spherically-configured head section 14 of holder 10 of the implant in a force-fit lock. The push/pull system essentially comprises the following components: a coil spring 106, through the interior of which an actuator means 107 extends which is rigid in the axial direction yet still sufficiently flexible, a shaft 111 of gripper tongs 102 being affixed at its proximal end and a first gripping section 108 disposed at its distal end. The push-pull system additionally comprises a taper sleeve 109 which receives the shaft 111 of the axially-displaceable gripper tongs 102 at its proximal end section 112 and the proximal end of the coil spring 106 at its distal end section 113 by abutting against a stop 114. The push-pull system additionally and essentially comprises a second gripping section 110, at which the distal end of the coil spring 106 is received by abutting against a stop, whereby gripping jaws 103, 104, 105 close from the force exerted by the coil spring 106 on the outer adjacent proximal frontal end 115 of the taper sleeve 109 and open as a result of the forward advancing of the actuator means 107. As a particularly essential component, said surgical instrument 100 has an insertion thread or guidewire 116 which extends out of gripper tongs 102 in the delivery state of surgical instrument 100 from its proximal end in the form of a loop 117 and which is guided by the two loose ends 118, 119 through the interior of taper sleeve 109 and the interior of coil spring 106 to a first gripping section 108 at the distal end of surgical instrument 100, whereby loop 117 can be introduced through eyelet 16 of holder 10 prior to the implantation of the implant and affixed to gripper tongs 102 at a fix point 101. Insertion thread or guidewire 116 exhibits a first loose end 119 attachable in the area of the first gripping section 108 and a second loose end 118 which is provided with a nipple 120, with the help of which the insertion thread/guidewire 116 can either be stretched out in the coupled state of the implant or be retracted from the surgical instrument 100 after the connection between the first end 119 and the first gripping section 108 has been disengaged. Said retracting of the insertion thread/guidewire from surgical instrument 100 does not occur until the implanted occlusion device exhibits the exact seating as desired by the surgeon. Should this not be the case, the insertion thread/guidewire 116 serves in readily allowing the surgeon to re-connect gripping tongs 102 of surgical instrument 100 to the head section 14 of holder 10 of occlusion device 1; i.e., gripping jaws 103, 104, 105 of gripper tongs 102 can grab spherical-shaped head section 14 of holder 10 securely and in form-fit fashion.

Figure 3:
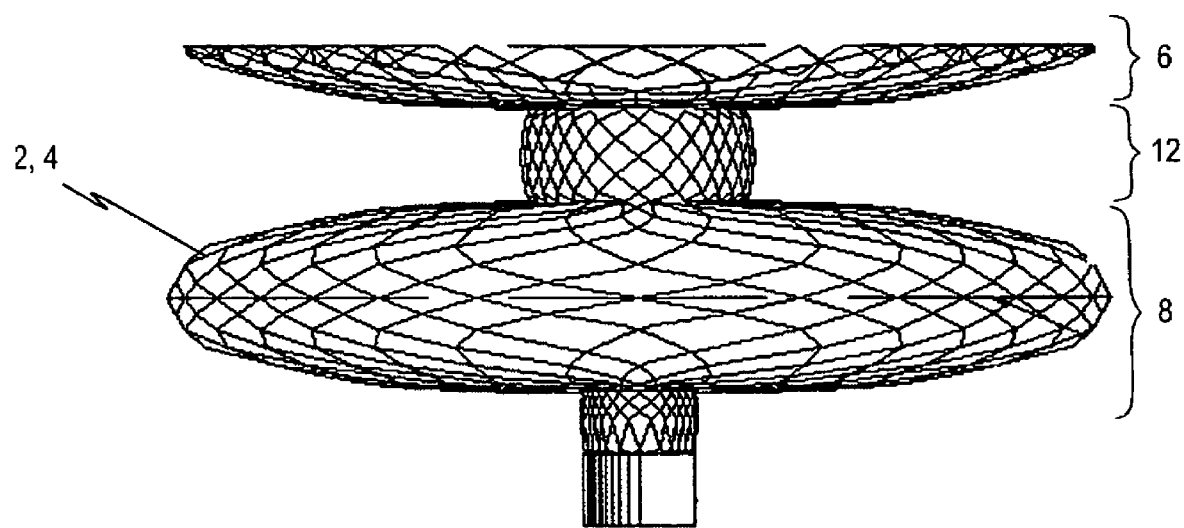
FIG. 3 shows a perspective representation of an occlusion device embodiment.

FIG. 3 shows an example of an occlusion device which can be provided with an inventive holder 10. This occlusion device essentially consists of a braiding 2 of thin wires or threads 4 which is given a suitable final form by means of a molding and heat treatment procedure and which tapers to the diameter of a catheter 5 used for an intravascular implanting or explanting surgical procedure. Said occlusion device comprises a proximal retention area 6 and a distal retention area 8 at which the ends of the wires or threads 4 converge into a holder 10, as well as a cylindrical crosspiece 12 between said proximal retention area 6 and said distal retention area 8, whereby the two retention areas 6, 8 position on the two sides of a shunt to be occluded in a septum following implantation while the crosspiece 1 transverses the shunt. The occlusion device is thus particularly suited to treating septum defects with the device able to be introduced to the defect to be occluded via a catheter 5. Because the proximal retention area 6 of braiding 2 exhibits a single-layered, plate-shaped flattening toward the proximal end of the occlusion device, this allows the occlusion device to adjust automatically to the septal defect in particularly advantageous manner—independent of the relative diameter of the defect to be occluded and independent of the thickness of the septal wall—and to do so with no part of the occlusion device projecting beyond the plane of the septal wall with the defect at the proximal side of the defect. There is thus no occurrence of the usual complications which normally arise in such cases. In other words, this means that the occlusion device is ingrown by the body's own tissue substantially faster than is the case with the occluding systems known in the prior art.

Using a braiding composed of thin wires or threads as the starting material for the inventive occlusion device yields the further advantage of long-term mechanical stability. This thus largely prevents structural fractures in the inserted implant. The braiding moreover has sufficient rigidity. The plate-shaped hub-less profile to braiding 2 toward the proximal end additionally allows the proximal retention area 6 of the occlusion device to flatten completely against the lateral edge of the defect in the inserted state. As a result, the occlusion device can be used for a wide range of differently sized septal defects. Since braiding 2 tapers to the diameter of a catheter used in intra-vascular surgery, it is possible to introduce the occlusion device through e.g. a vein, such that it is no longer necessary to perform an open operation in the literal sense. Because braiding 2 is made from a material which has "memory" effect, the occlusion device can also be termed a "self-expanding device" which, upon exiting the catheter, unfolds by itself such that the two retention areas 6, 8 can position accordingly on the proximal/distal sides of the defect.

Figure 4:
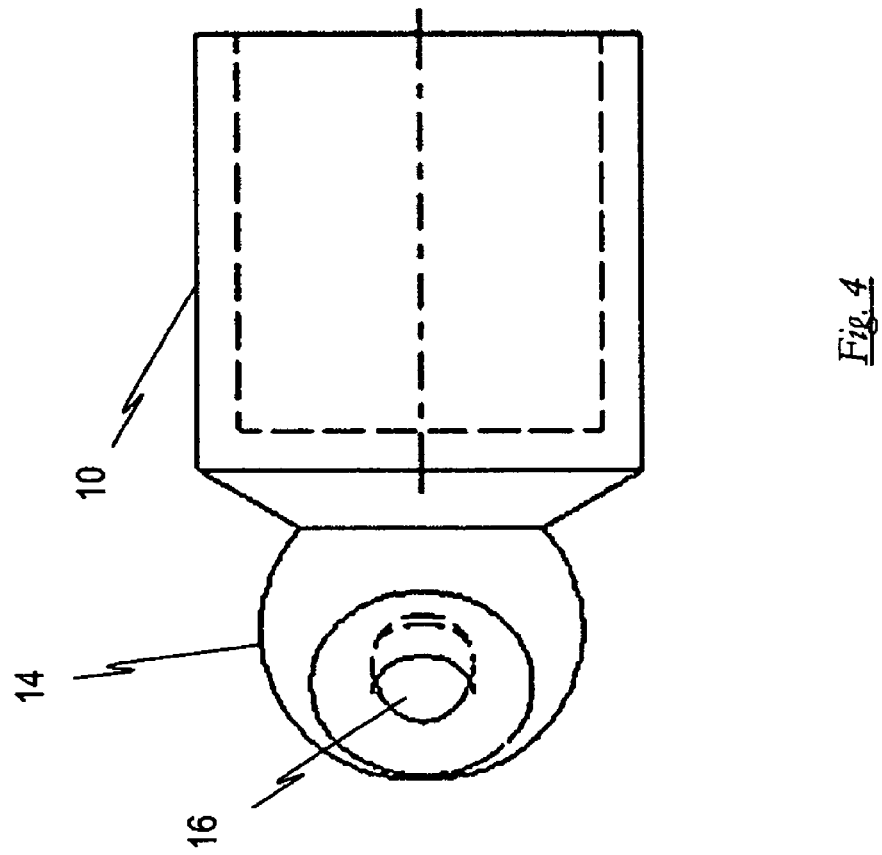
FIG. 4 shows an enlarged side view of a first embodiment of a holder for the occlusion device.

FIG. 4 shows an enlarged side view of a first embodiment of a holder 10 of such an occlusion device. This holder 10 exhibits a head section 14 at its free end having an eyelet 16 in the form of a cross-hole, whereby head section 14 can be gripped and held by surgical instrument 100 in form-fit fashion.

Figure 5:
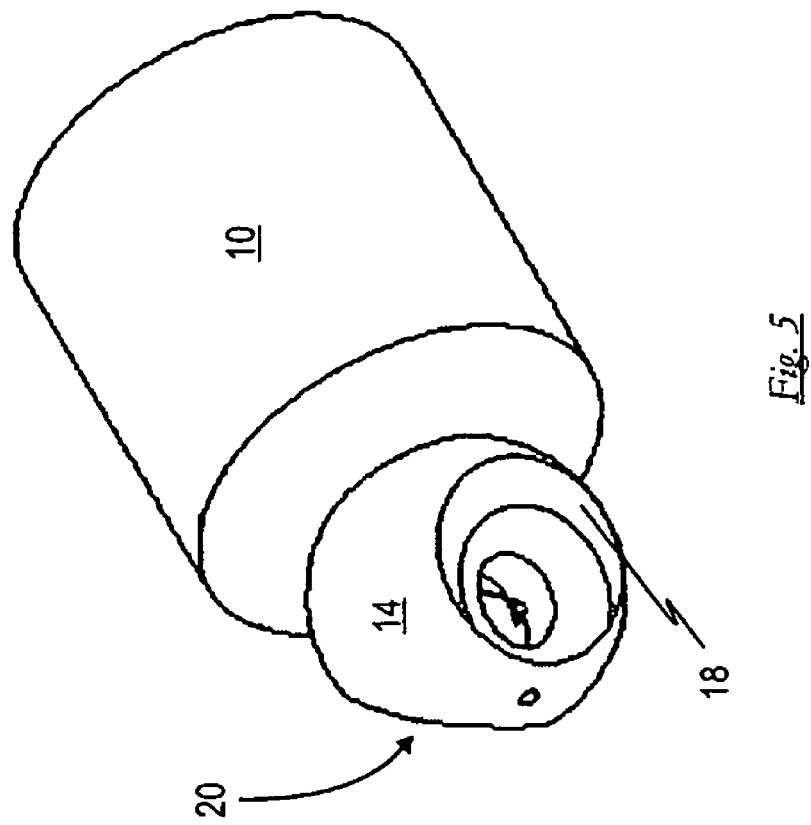
FIG. 5 shows a perspective representation of the holder pursuant to FIG. 4.

FIG. 5 shows a perspective representation of the holder according to FIG. 4. This representation helps to illustrate how the dual-sided cut discharge surface 18, 20 of the cross-hole is configured to converge with the outer surface of the spherical head toward the free end of holder 10.

Figure 6:
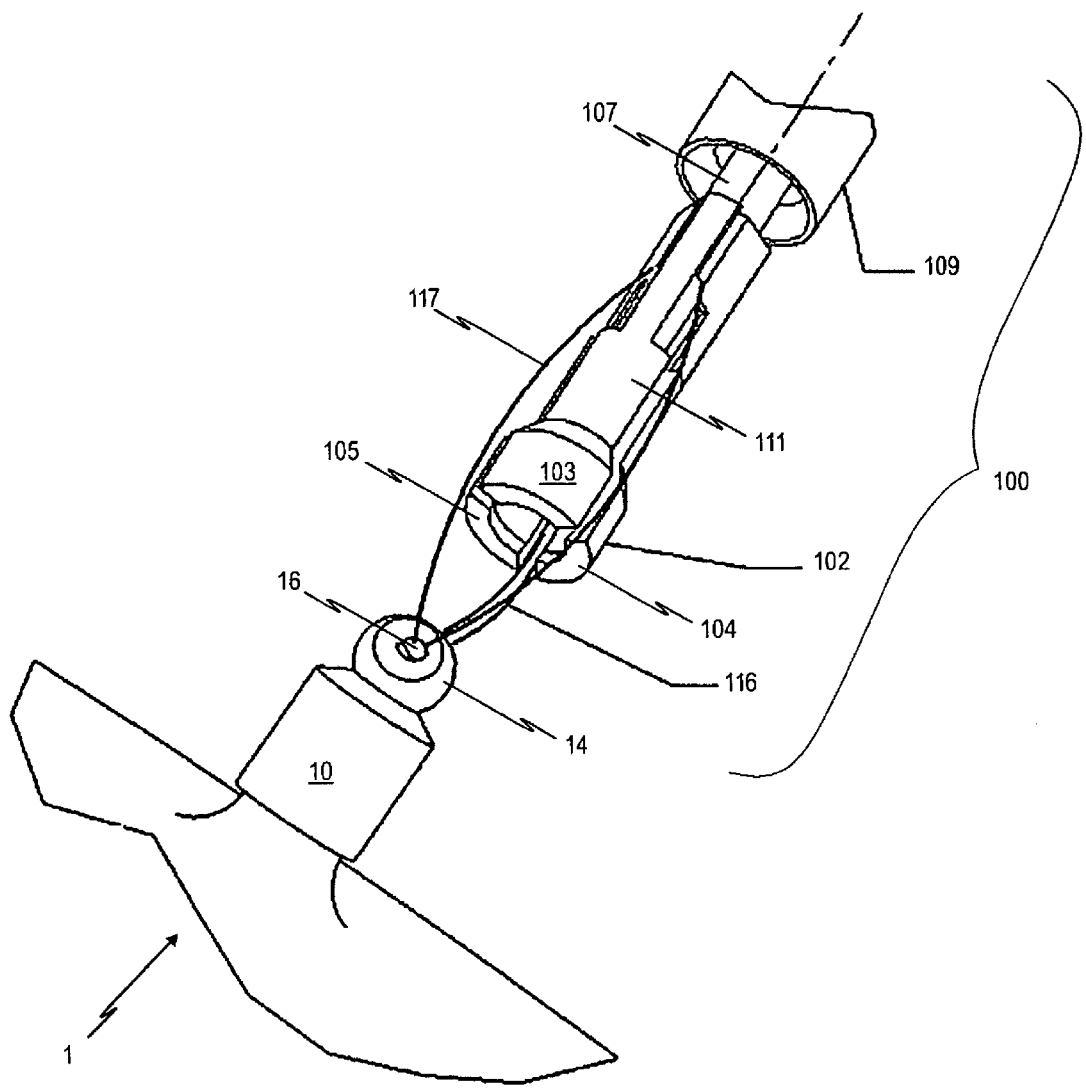
FIG. 6 shows an enlarged detail view of the gripper tongs of an occlusion device including guidewire and holder.

FIG. 6 shows an enlarged detail view of surgical instrument 100 with guidewire 116 extending through eyelet 16 which is hooked in the form of a loop 117 at shaft 111 of gripper tongs 102 (cf. FIG. 2, fix point 101). This representation helps to illustrate how gripper tongs 102 are provided with an outer tapering at the front and divided into three gripping jaws 103, 104, 105 by means of longitudinal grooves which close upon positioning of the tapered shaft at the proximal forward end 115 of taper sleeve 109. Gripping jaws 103, 104, 105 are hereby rotated to reflect the shape of a bowl in order to force-fit grip the spherical head section 14 of holder 10. Shaft 111 of gripper tongs 102 is of flattened configuration in order to guide loop 117 of insertion thread/guidewire 116 through taper sleeve 109. Loop 117 is prepared such that it will protrude from gripper tongs 102 in the delivery state (see FIG. 7). The loose ends 118, 119 of insertion thread/guidewire 116 are guided through the slot in gripper tongs 102 and through coil spring 106 and fastened at the first gripping section 108 of the grip, whereby the second loose end 118 is additionally provided with a nipple 120 which facilitates the gripping and tensioning of the insertion thread/guidewire.

Figure 7:
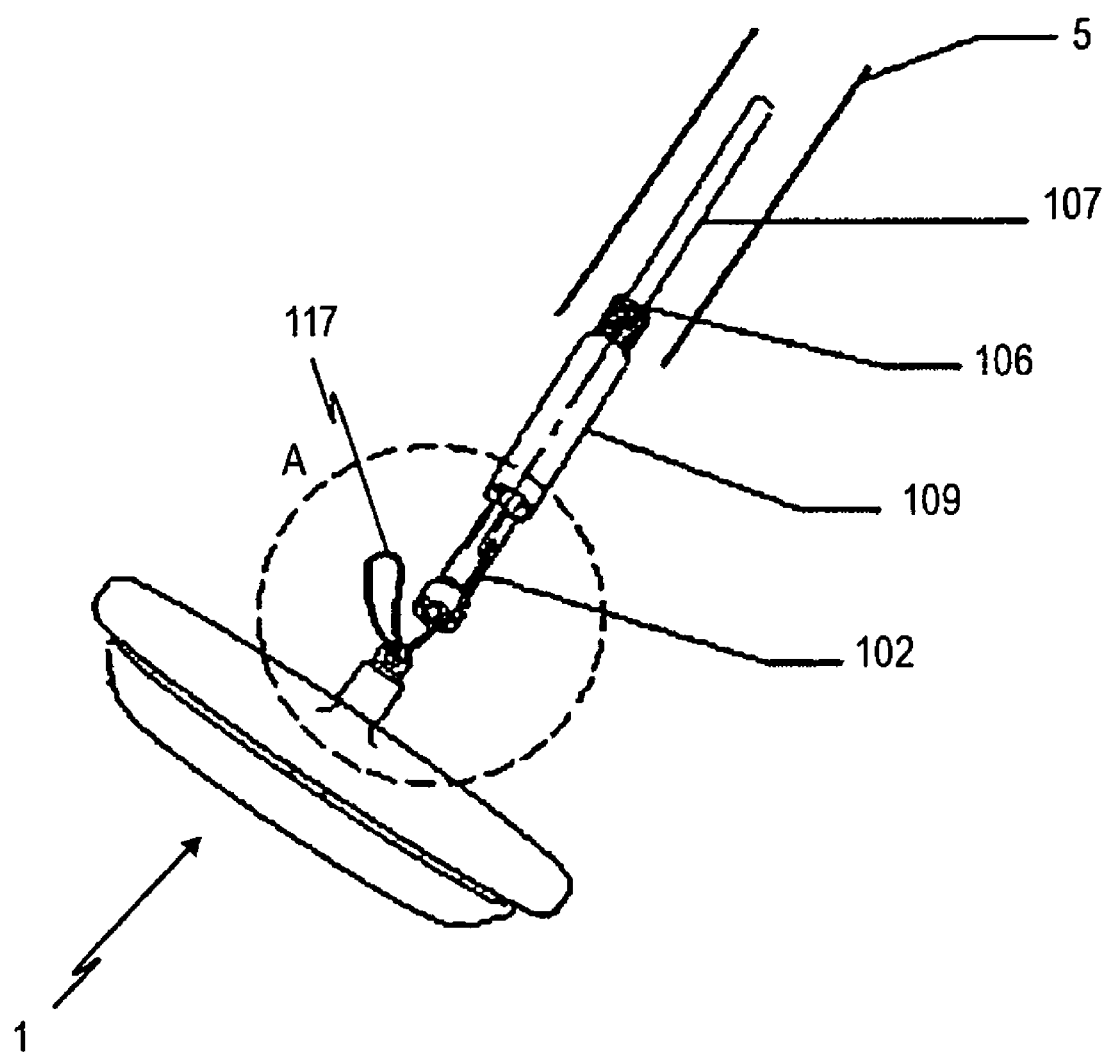
FIG. 7 shows a view of the forward section of the surgical instrument and an occlusion device having a loop pulled through same.

FIG. 7 depicts a simplified view of the forward section of surgical instrument 100 comprising the taper sleeve 109, gripper tongs 102, coil spring 106 and actuator means 107. Loop 117 of insertion thread/guidewire 116 can be seen in front of gripper tongs 102 and already fed through eyelet 16 of head section 14 of holder 10. The section emphasized by the "A" circle represents the enlarged detail view in accordance with FIG. 6.

To couple occlusion device 1, loop 117 of insertion thread/guidewire 116 is pulled through eyelet 16 and hooked to a fix point 101 provided for the purpose on shaft 111 of gripper tongs 102 (see FIG. 2). The thread or wire material comprising loop 117 of insertion thread/guidewire 116 thereby extends through each respective slot between gripping jaws 103, 104 and 105 while the returning ends run through the third slot between gripping jaws 104, 105. When gripper tongs 102 are retracted in taper sleeve 109 by tightening insertion thread/guidewire 116, loop 117 can no longer hang on. Loop 117 is then pulled so far toward nipple 120 until the spherical head section 14 of holder 10 sinks into the gripping jaws 103, 104, 105 of gripper tongs 102. The other end 119 of insertion thread/guidewire 116 not disposed with the nipple 120 is fastened appropriately in the area of second gripping section 108.

A method for the repeatable coupling of an implant with a holder 10 as described above, in particular of an occlusion device 1, to surgical instrument 100 will be described in the following.

In a first step, loop 117 of insertion thread/guidewire 116 is guided through eyelet 16 of holder 10 of the implant prior to beginning the intravascular procedure and hooked on a fix point 101 provided for the purpose on gripper tongs 102 while the first and second loose ends 119, 118 of insertion thread/guidewire 116 are held or fastened in the area of first gripping section 108. In a second step, head section 14 of holder 10 of the implant is grabbed by gripping tongs 102. In a third step, the second loose end 118 of insertion thread/guidewire 116 provided with nipple 120 is tightened until head section 14 is fully accommodated within gripping jaws 103, 104, 105. Releasing the second loose end 118 provided with the nipple prompts the releasing of gripping tongs 102 from head section 14 of the implant and the seating of the implant is checked. Insertion thread/guidewire 116 allows gripper tongs 102 to recouple to holder 10 of the implant at any time.

Figure 8:
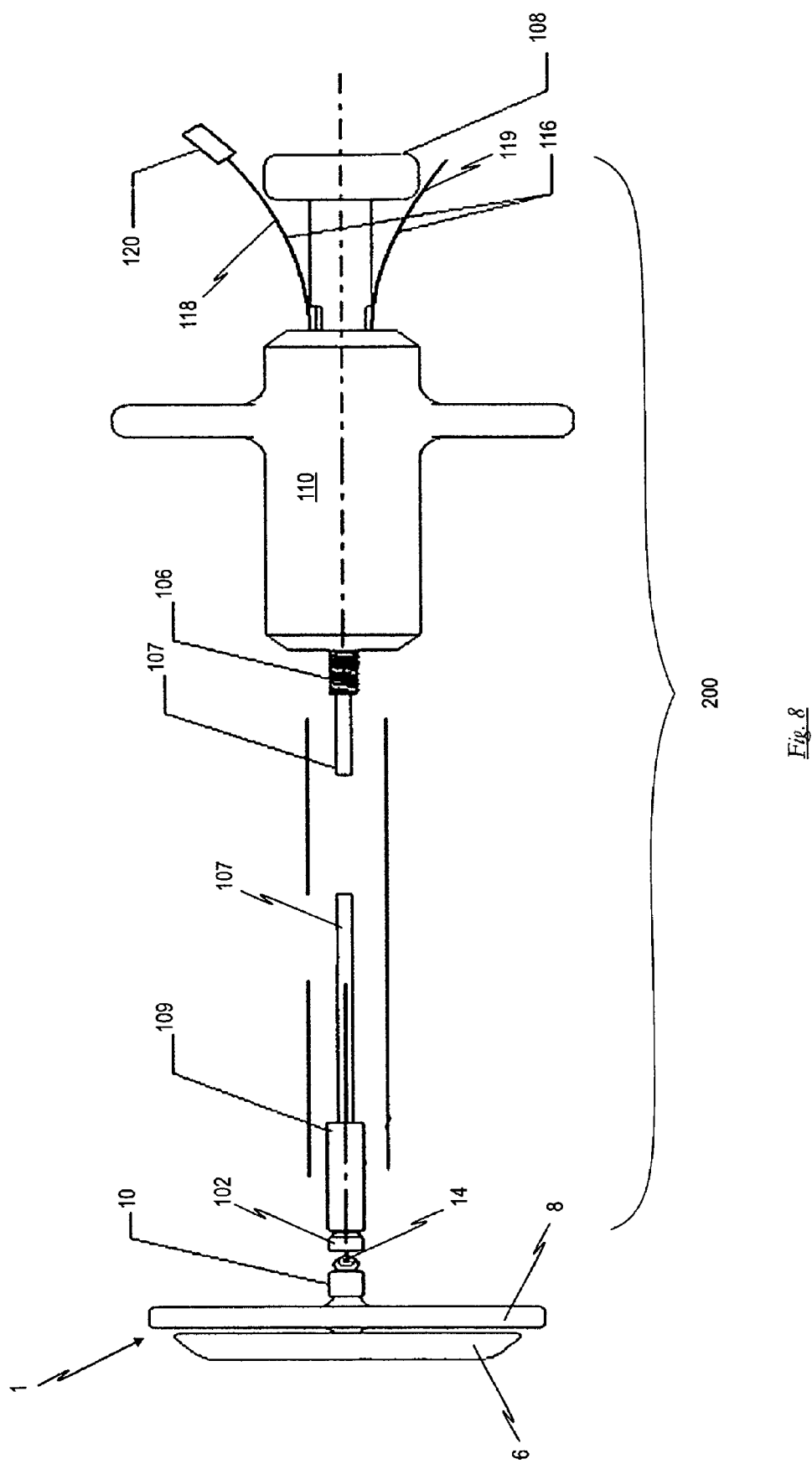
FIG. 8 shows a side view of a surgical instrument with an occlusion device at the insertion thread/guidewire in accordance with a second embodiment.
Figure 9:
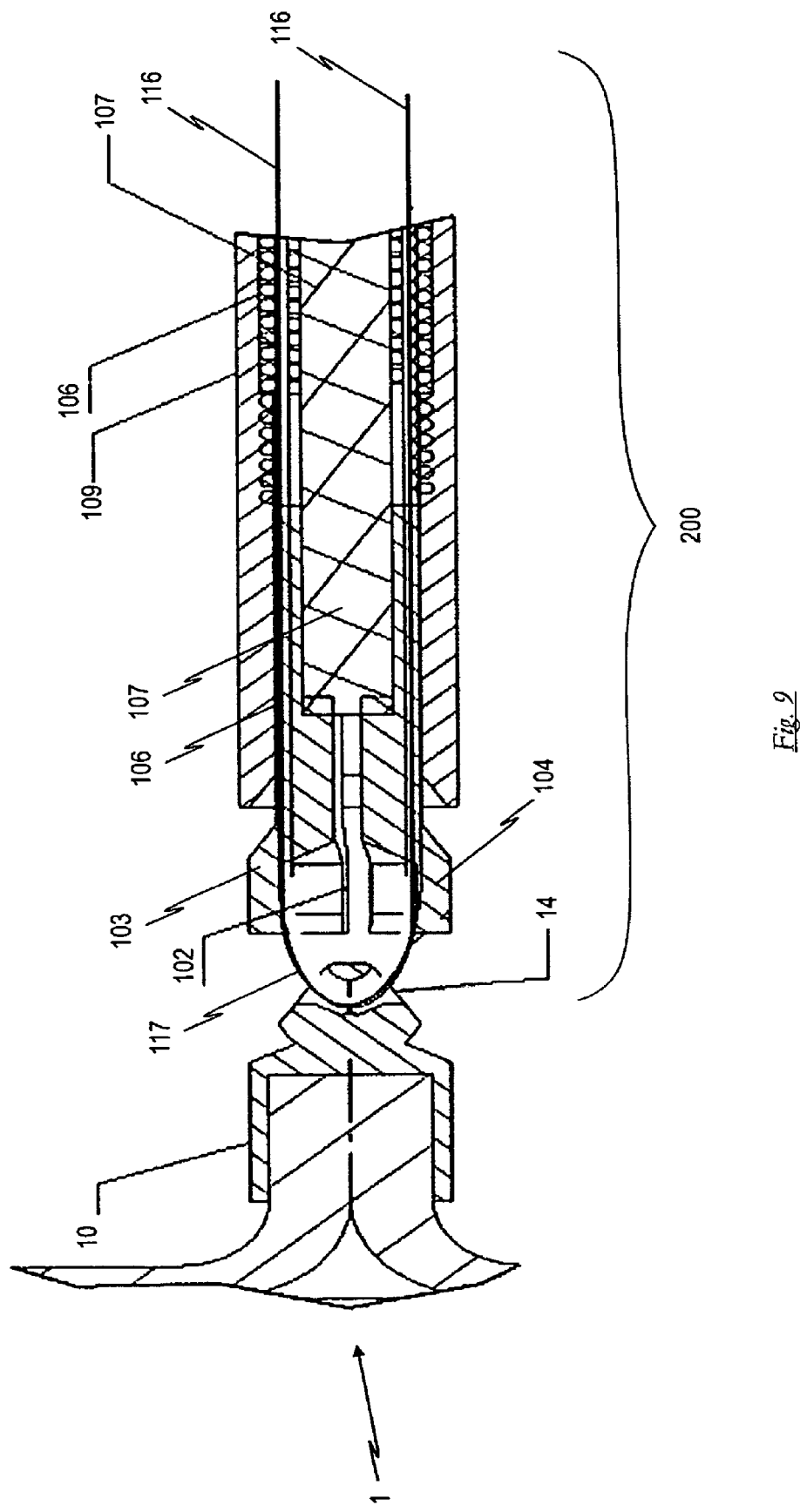
FIG. 9 shows a sectional detail view of the forward section of the surgical instrument with the occlusion device at the insertion filament/wire pursuant to FIG. 8.

FIGS. 8 and 9 show a condensed side view and a detail view of a second embodiment of a surgical instrument 200 with an occlusion device 1 to be coupled thereto, exhibiting a holder 10 of a second embodiment of the present invention. The reference numerals from FIGS. 1 and 2 are again repeated here to identify the same components to surgical instrument 200 and occlusion device 100. The difference between this second embodiment of occlusion device 1, the second embodiment of surgical instrument 200 respectively, and the same components of the first embodiment lies in the configuration of the head section 14 of holder 10 of occlusion device 1 and in how the insertion thread/guidewire 116 is used and guided, which becomes clear when viewing FIG. 9: in same, loop 117 of insertion thread/guidewire 116 is not guided through eyelet 16 of head section 14 with the two threads or wires but rather only one thread runs through said eyelet 16 and is otherwise led by its two loose ends 118, 119 through the interior of taper sleeve 109 and the interior of coil spring 106 to first gripping section 108 at the distal end of surgical instrument 200. the connecting of insertion thread/guidewire 116 to head section 14 of holder 10 will be described in the following by making reference to FIGS. 10 and 11.

FIGS. 10 and 11 show an enlarged side view (FIG. 10) and a perspective representation respectively (FIG. 11) of a second embodiment of a holder 10 of an occlusion device 1. This second embodiment differs from the first embodiment pursuant FIGS. 4 and 5 in that eyelet 16 of head section 14 is slit diagonal to the cross-hole, whereby the ends 22, 24 of diagonal slot 26 overlap with respect to the longitudinal direction of the cross-hole. Other than that, this second embodiment of head section 14 likewise exhibits a spherical head and the dual-sided cut discharge surface 18, 20 of the cross-hole is preferably configured to converge with the outer surface of the spherical head toward the free end of holder 10. Since eyelet 16 has a diagonal slot 26, loop 117 of insertion thread/guide-wire 116 can be moved into eyelet 16 without needing to loop a loose end 118, 119 of the insertion thread through eyelet 16 or even pass the entire loop 117 through eyelet 16 to hook onto shaft 111 of gripping tongs 102. Diagonal slot 26 thus enables an especially easy hooking of loop 117.

Eyelet 16 yields the advantage that loop 117 can be removed at any time in the same way, namely by the surgeon upon determining that occlusion device 1 is properly seated and surgical instrument 200 is to be ultimately disengaged from occlusion device 1. To do so, loop 117 is withdrawn from eyelet 16 and from the entire surgical instrument 200 as in the first embodiment by pulling on one of the loose ends 118, 119, preferably, however, the second loose end 118 provided with nipple 120.

Figure 12:
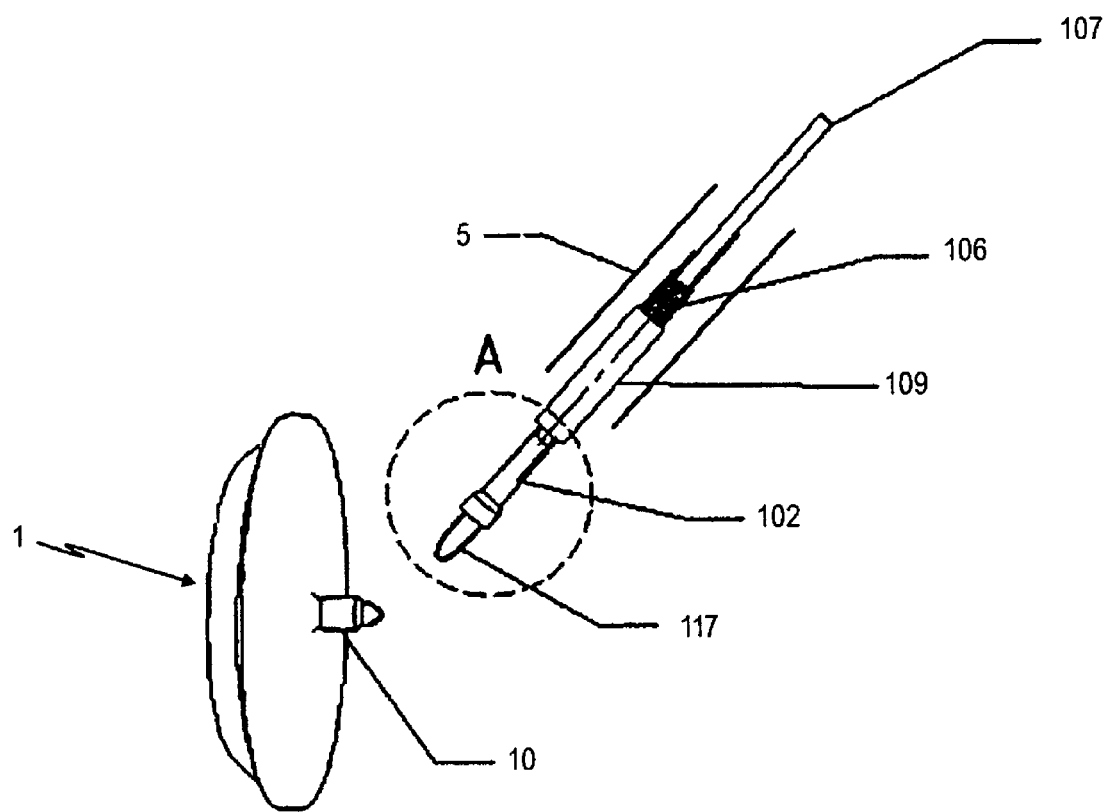
FIG. 12 shows a simplified view of the forward section of the surgical instrument with gripper tongs, insertion thread/guidewire and occlusion device.

FIG. 12 shows a simplified representation of the forward section of surgical instrument 200 with loop 117 protruding from the tip of gripper tongs 102 and the occlusion device 1 to be coupled, all in accordance with the second embodiment.

Figure 13:
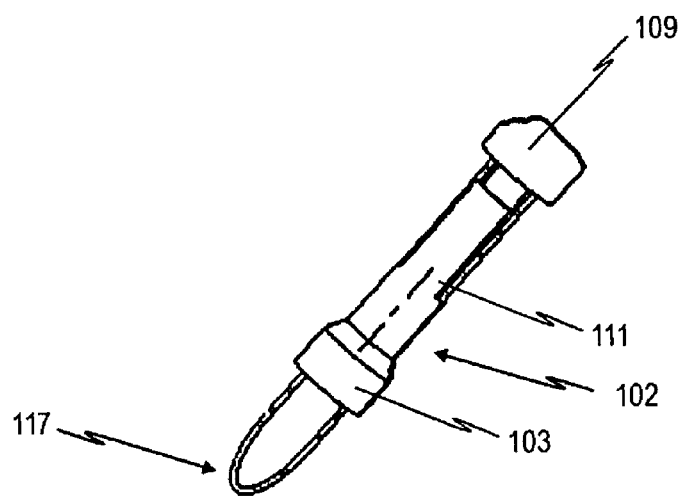
FIG. 13 shows an enlarged detail view of the "A" section pursuant to FIG. 12.

FIG. 13 shows an enlarged detail view of gripper tongs 102 with loop 117 of insertion thread/guidewire 116 protruding from between gripping jaws 103, 104, 105 (gripping jaws 104, 105 are not visible in this representation).

Figure 14:
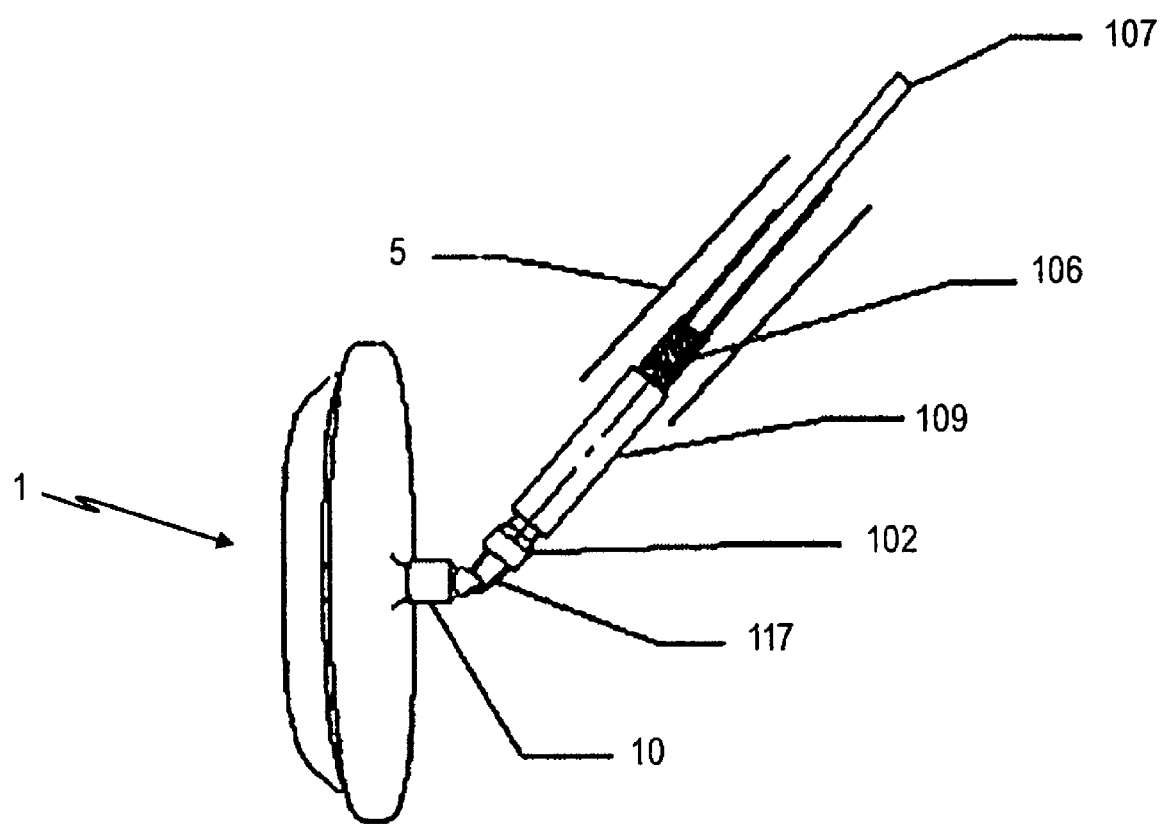
FIG. 14 shows a view of the forward section of the surgical instrument with gripper tongs and occlusion device with hooked guidewire loop.

FIG. 14 shows a representation similar to that of FIG. 12, wherein FIG. 14 shows surgical instrument 200 already having been connected to occlusion 1.

The push/pull system of the second embodiment of surgical instrument 200 consists of the same components as was described above with respect to the first embodiment.

The method for the repeatable coupling of an implant having a holder 10 of the second embodiment, an occlusion device 1 in particular, to a surgical instrument 100 in accordance with the second embodiment will be described in the following: in a first step, loop 117 of insertion thread/guidewire 116 is guided through diagonal slot 26 in eyelet 16 of holder 10 of the implant prior to beginning the intravascular procedure while the first and second loose ends 119, 118 of insertion thread/guidewire 116 are held or fastened in the area of first gripping section 108. In a next step, head section 14 of holder 10 is grabbed by gripper tongs 102. The second loose end 118 of insertion thread/guidewire 116 provided with nipple 120 is then tensioned until the head section 14 is fully accommodated within gripping jaws 103, 104, 105. Loosening the second loose end 118 provided with nipple 120 allows the releasing of gripper tongs 102 from head section 14 of the implant and the seating of the implant can be checked. Insertion thread/guidewire 116 allows gripper tongs 102 to recouple to holder 10 of the implant at any time. If occlusion device 1 is to be ultimately disengaged from surgical instrument 200, insertion thread/guidewire 116 is withdrawn from the surgical instrument by pulling on the second loose end 118 provided with nipple 120. During the extracting, it is important for loop 117 to be flexible enough to wind around the tight radii and for there to be no sharp edges to the deflection points on the eyelet 16 or gripper tongs 102. With respect to eyelet 16, same is secured as described above in that the dual-sided cut discharge surface 18, 20 of the cross-hole is configured to converge with the outer surface of the spherical head toward the free end of holder 10. Moreover, using thin, super-elastic nitinol wire as the insertion thread/guidewire 116 is particularly suitable, even though surgical suture may also be used.

Figure 15:
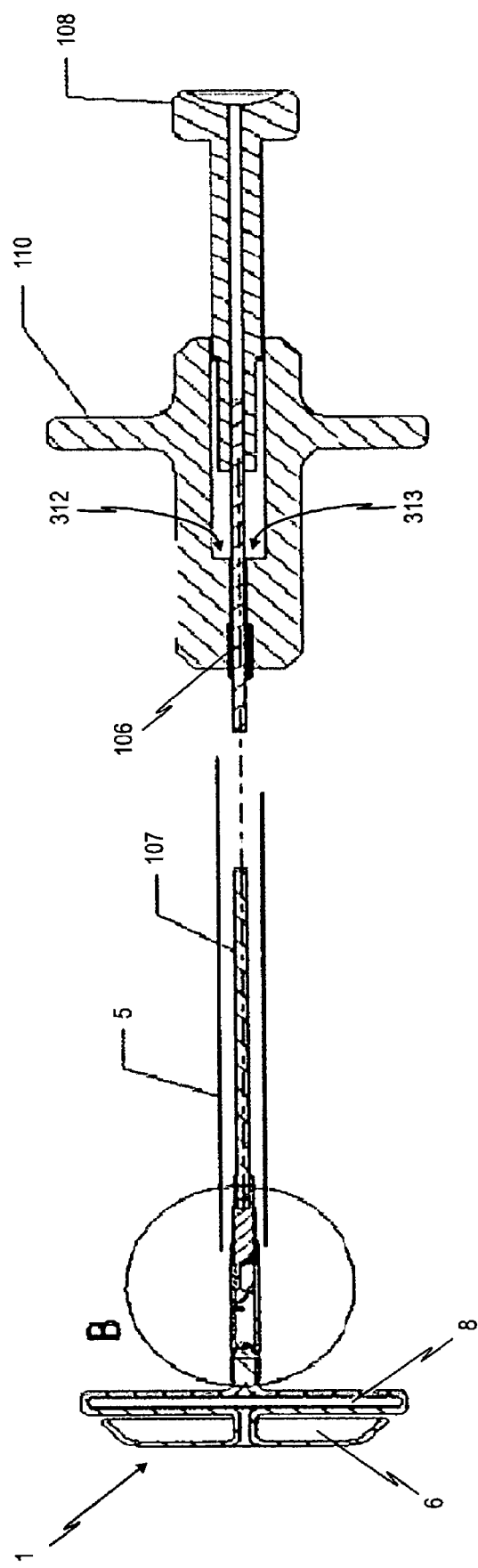
FIG. 15 shows a compressed sectional representation of a surgical instrument with hooked occlusion device in accordance with embodiment 3.
Figure 16:
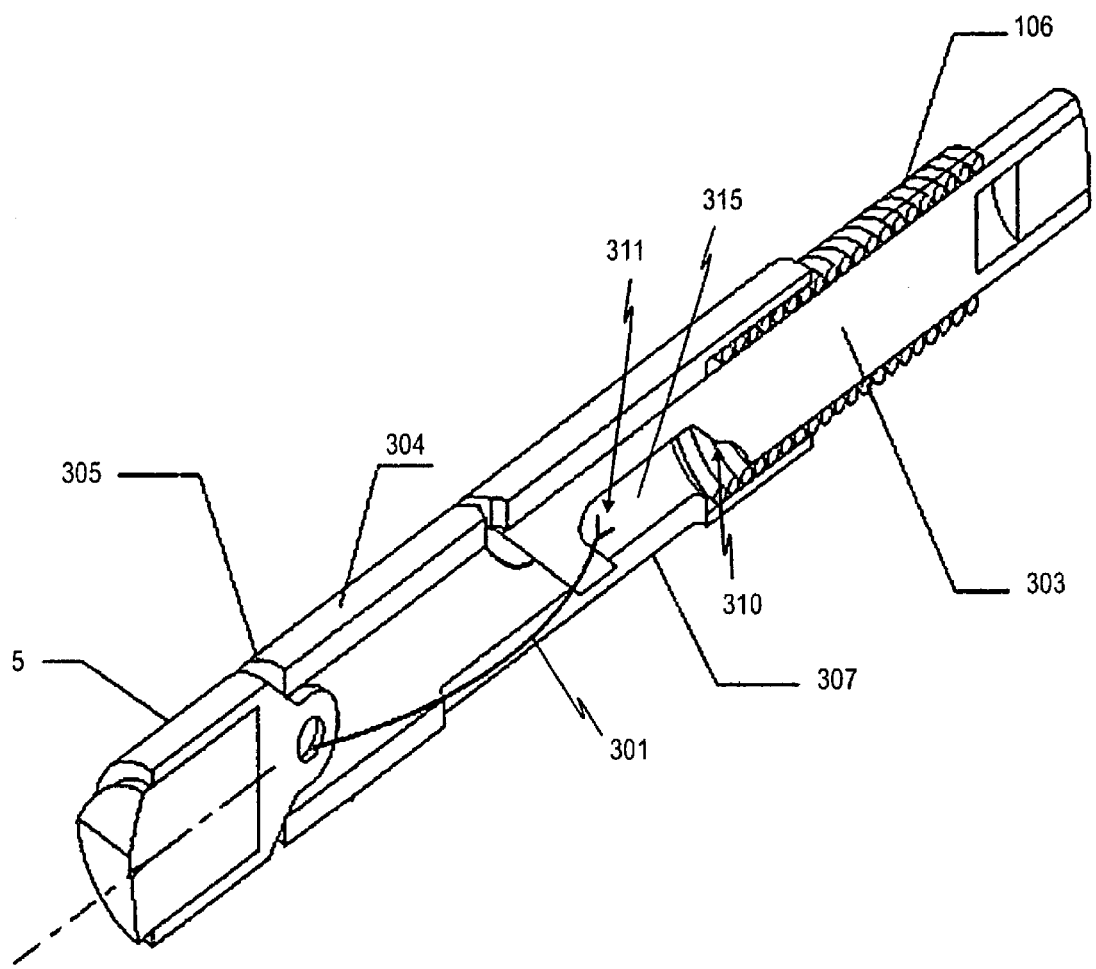
FIG. 16 shows a sectional detail view pursuant "B" from FIG. 15.
Figure 17:
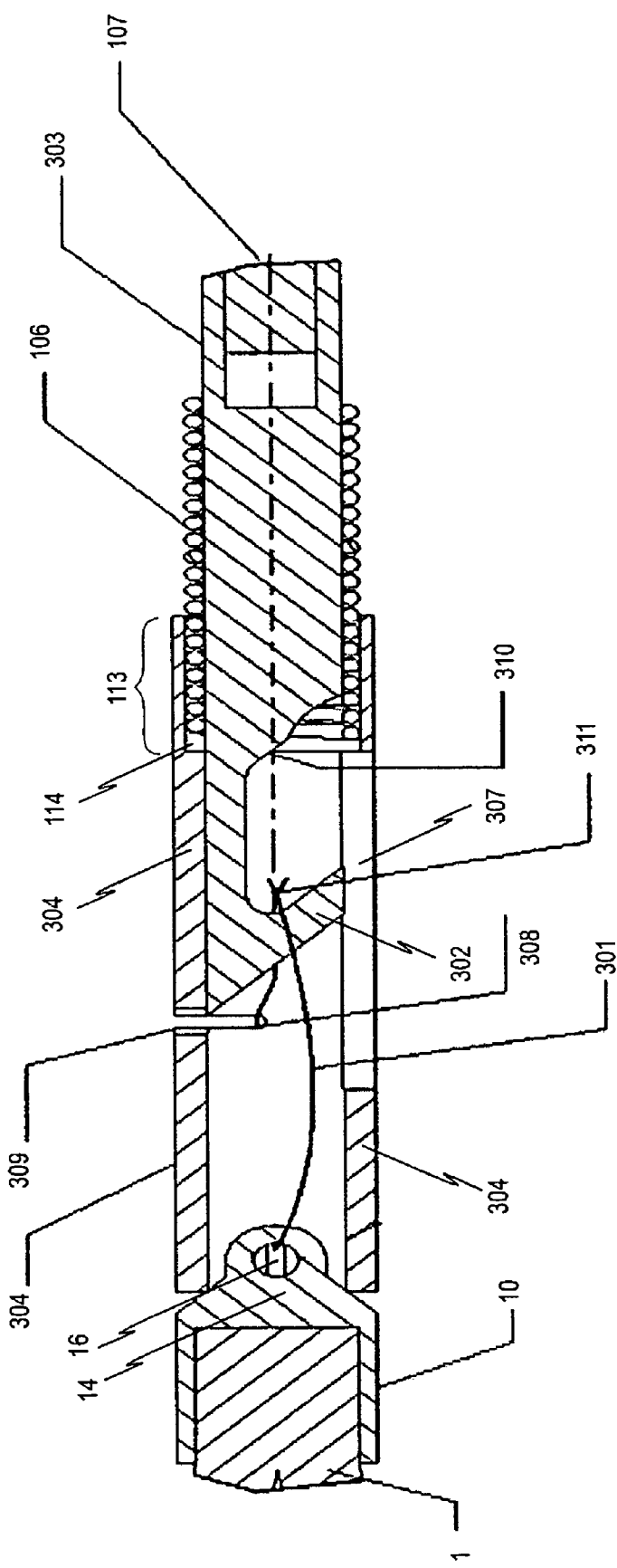
FIG. 17 shows a section through the forward section of the surgical instrument with coupled occlusion device.

FIGS. 15, 16 and 17 show a compressed sectional representation (FIG. 15), a perspective detail representation pursuant the "B" circle of FIG. 15, and a sectional representation through the forward region of a surgical instrument 300 with an occlusion device 1, all of the third embodiment. Surgical instrument 300 essentially exhibits a hook 302 which is axially movable toward and away from eyelet 16 of head section 14 of holder 10 of occlusion device 1 by means of a push-pull system as well as a fastening loop 301 extending through eyelet 16 and fixable at hook 302, by means of which the implant can be held to surgical instrument 300 through the tensioning of fastening loop 301 when hook 302 is moved away from eyelet 16. In this case, the push/pull system consists essentially of the following components: a spiral coil 106, an actuator means 107 extending axially through the interior of the latter which is sufficiently rigid in the axial direction yet still sufficiently flexible, with a shaft of hook 302 attached to its proximal end as well as a first gripping section 108 at its distal end. The push-pull system moreover essentially exhibits a cylindrical sleeve 304 for receiving the proximal end of coil spring 106 at its distal end section 113 by abutting against a stop 114 and in which shaft 303 of hook 302 is accommodated in axially-displaceable fashion. Lastly, this push/pull system of this said third embodiment includes another second gripping section 110 at which the distal end of the coil spring 106 is received by abutting against a stop, whereby hook 302 is moved away axially from eyelet 16 by the force exerted by coil spring 106 which can be moved toward eyelet 16 by the forward advancing of actuator means 107.

Figure 19:
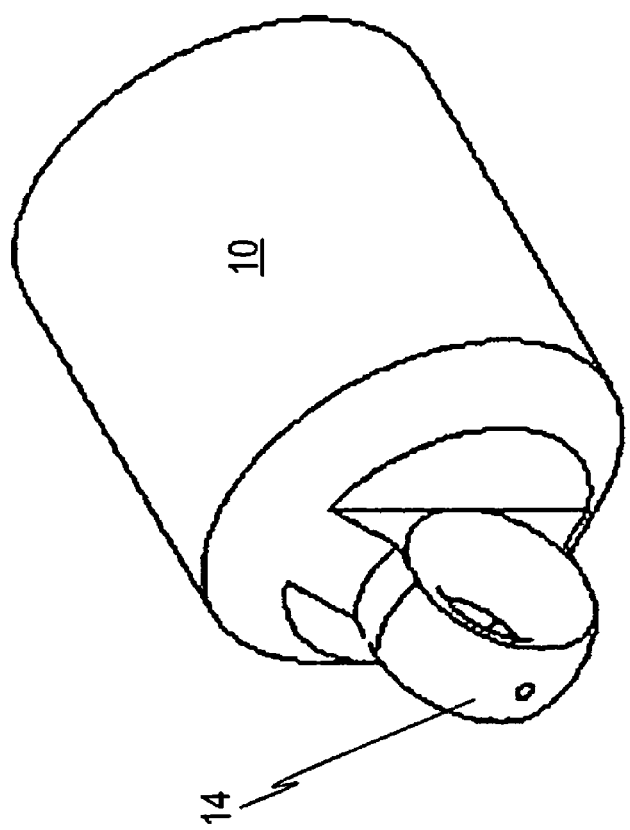
FIG. 19 shows a perspective representation of the holder pursuant to FIG. 18.
Figure 18:
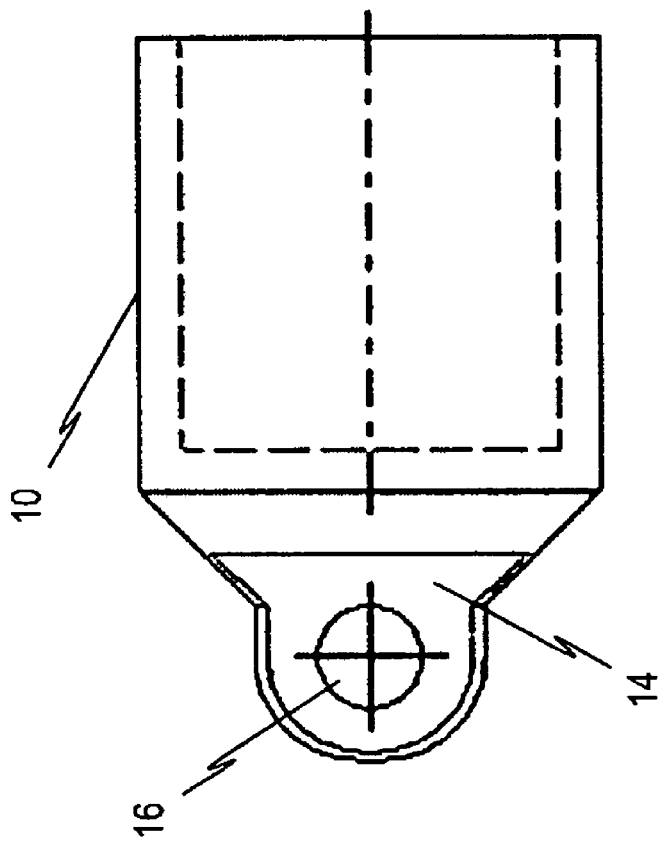
FIG. 18 shows an enlarged side view of the holder of an occlusion device in accordance with embodiment 3.

FIGS. 18 and 19 respectively show an enlarged side view and an enlarged perspective representation of the third embodiment of a holder 10 of occlusion device 1. This third embodiment differs from the other two embodiments in that holder 10 exhibits a head section 14 at its free end configured as a centering sleeve having an eyelet 16 in the form of a semi-spherical cross-hole in longitudinal section and holder 10 can be held to surgical instrument 300 by means of a fastening loop 301 extending through eyelet 16 (cf. FIGS. 16 and 17).

Figure 20:
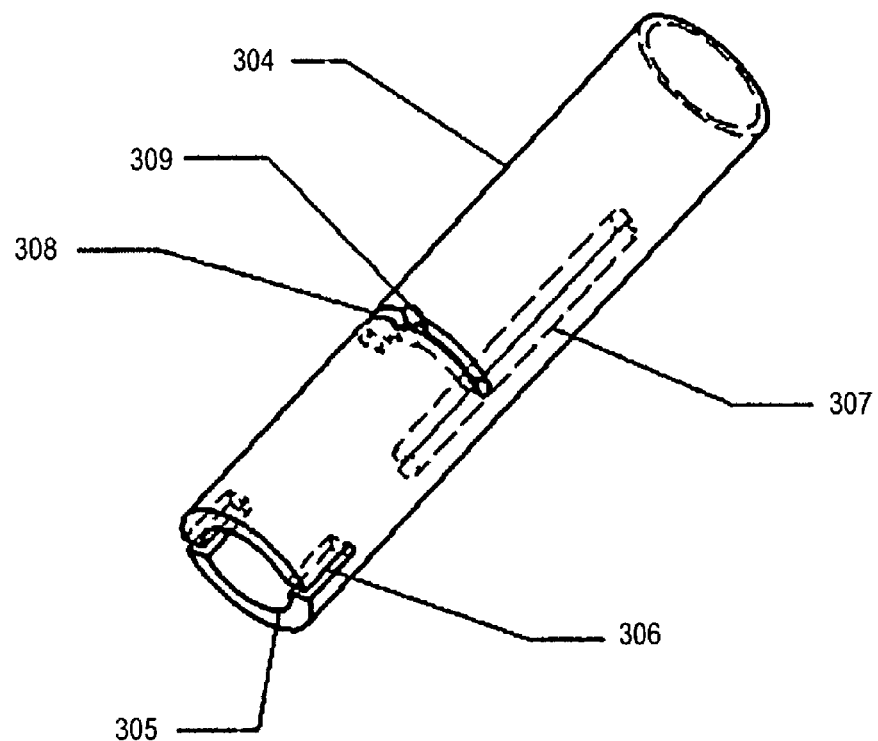
FIG. 20 shows an enlarged perspective representation of the cylindrical sleeve in accordance with embodiment 3.

FIG. 20 shows a perspective representation of cylindrical sleeve 304 of surgical instrument 300 in accordance with the third embodiment. Cylindrical sleeve 304 exhibits a continuous first longitudinal groove 306 at the proximal forward side 304, a second longitudinal groove 307 at one side of its center section for anti-twist guidance of the axially-displaceable hook 302 in the sleeve, and a cross-groove 308 at a right angle to the second longitudinal groove 307 on the one side which extends to the longitudinal axis of sleeve 304 and has a protrusion 309 at its center for receiving a knot 311 of fastening loop 301. The second longitudinal groove 307 is thus configured such that it cuts through the circumference of sleeve 304 from outer to inner diameter.

Figure 21:
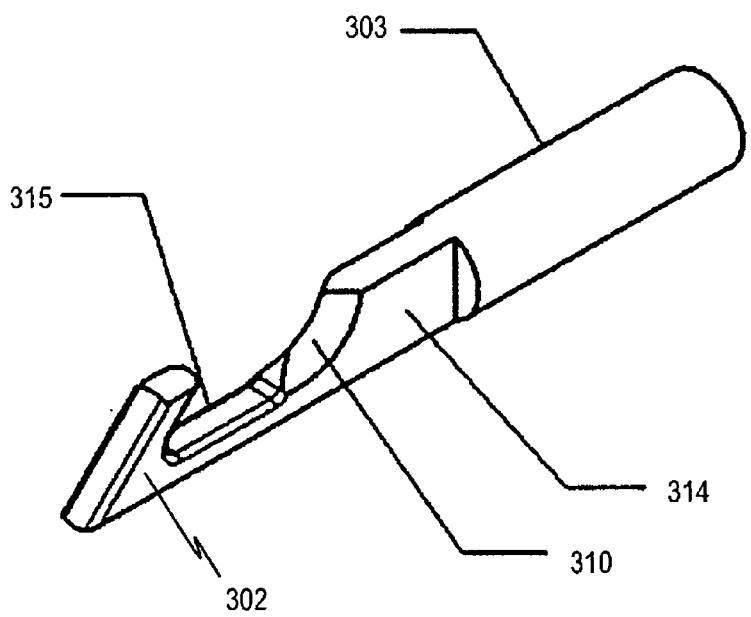
FIG. 21 shows an enlarged perspective representation of the hook pursuant to FIG. 17.

FIG. 21 shows a perspective representation of hook 302 with its shaft 303. The cross-section of the forward section of hook 302 is configured to be about one-third flatter than the cross-section of shaft 303, indicated by reference numeral 314. The flattened forward section of hook 302 thus fits with play into the second longitudinal groove 307 of cylindrical sleeve 304 (FIG. 20). A gap 315 of no material is configured behind the tip of hook 302, exhibiting a blade 310 at its distal end.

Figure 22:
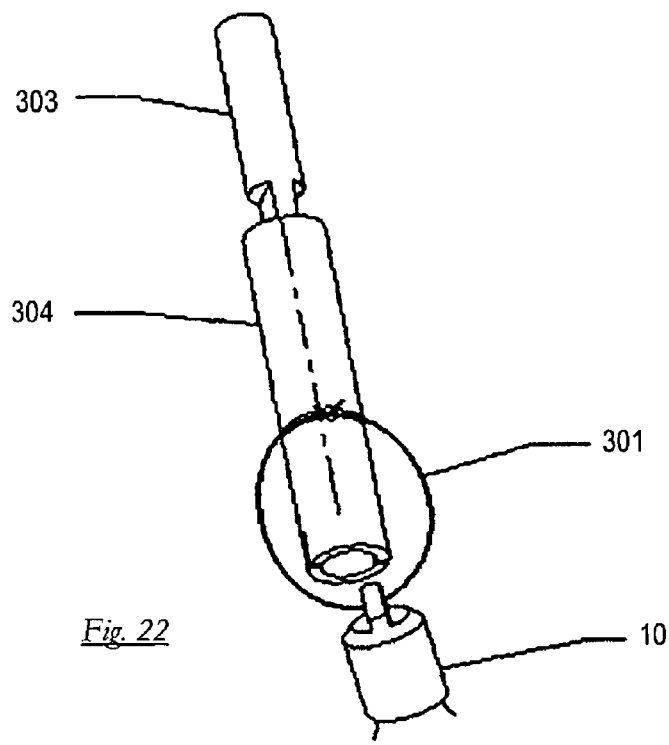
FIG. 22 shows a perspective representation of the forward section of the surgical instrument with the coupled holder of an occlusion device in accordance with the third embodiment.

FIG. 22 shows a perspective representation of the forward section of surgical instrument 300, which is unfixedly coupled to holder 10 of occlusion device 1 by means of fastening loop 301. Fastening loop 301 thus inserts into cross-groove 308 such that knot 311 of fastening loop 301 positions at protrusion 309 of cross-groove 308 while the thread of fastening loop 301 diametrically transverses cylindrical sleeve 304 in cross-groove 308. Cross-groove 308 is hereby configured such that knot 311 cannot break free laterally from the hooked fastening loop 301.

Figure 23:
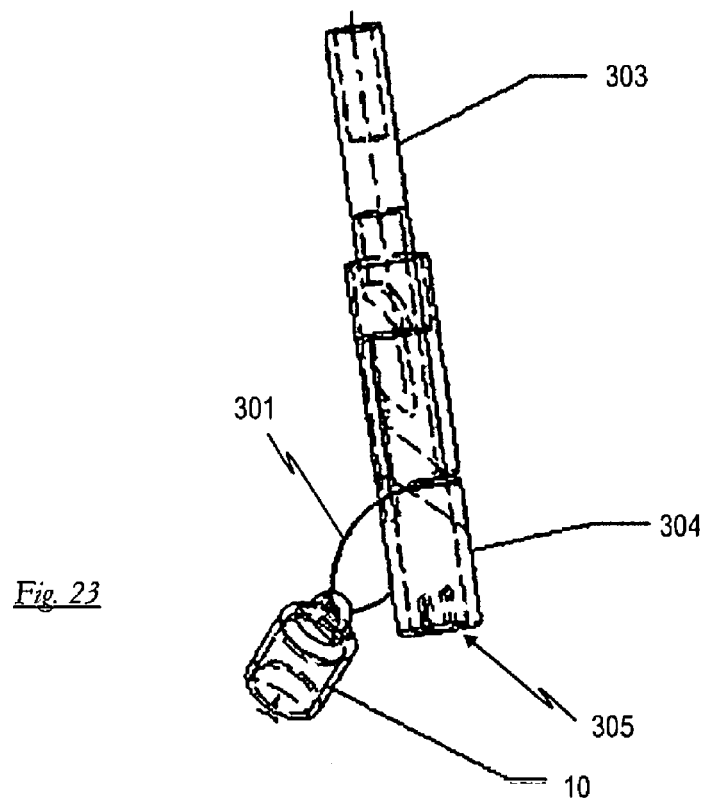
FIG. 23 shows a perspective representation similar to that of FIG. 22.

FIG. 23 shows a representation similar to FIG. 22, whereby the hook 302 inserted in cylindrical sleeve 304 is depicted with dashed lines. Upon a defined forward shifting of hook 302, fastening loop 301 basically slips over the tip of the hook from longitudinal groove 307 and remains in the gap 315 configured behind same. The knot of fastening loop 301 is situated in one of the side chambers formed by the flat section 314 of hook 302. Withdrawing hook 302 pulls occlusion device 1 with its holder 10 and the frontal side 305 of the cylindrical sleeve tight to surgical instrument 300. Fastening loop 301 thereby runs out from the continuous first longitudinal groove 306 at both sides and along the circumference of sleeve 304 until it is again guided along the cross-groove 308 inwardly and rearward of hook 302. Occlusion device 1 is thus coupled without play to the pull/pull system of surgical instrument 300 and can be inserted into a catheter 5 (not shown here).

For the final uncoupling of occlusion device 1 from surgical instrument 300, the stops 312, 313 disposed in the second gripping section 110 are released, whereby hook 302 can be pushed further forward a defined distance. The blade 310 arranged at the distal end of gap 315 behind the tip of the hook 302 is then activated. By withdrawing the surgical instrument, fastening loop 301 within cross-groove 308 is namely tensioned diametrically and can thus be separated by blade 310 by the forward displacement of hook 302. In consequence thereof, the end without a knot of fastening loop 301 separates from eyelet 16 of holder 10 upon withdrawal of surgical instrument 300, whereby the other end of fastening loop 301 with knot 311 ultimately remains within cross-groove 308 and thus on hook 302.

Figure 24:
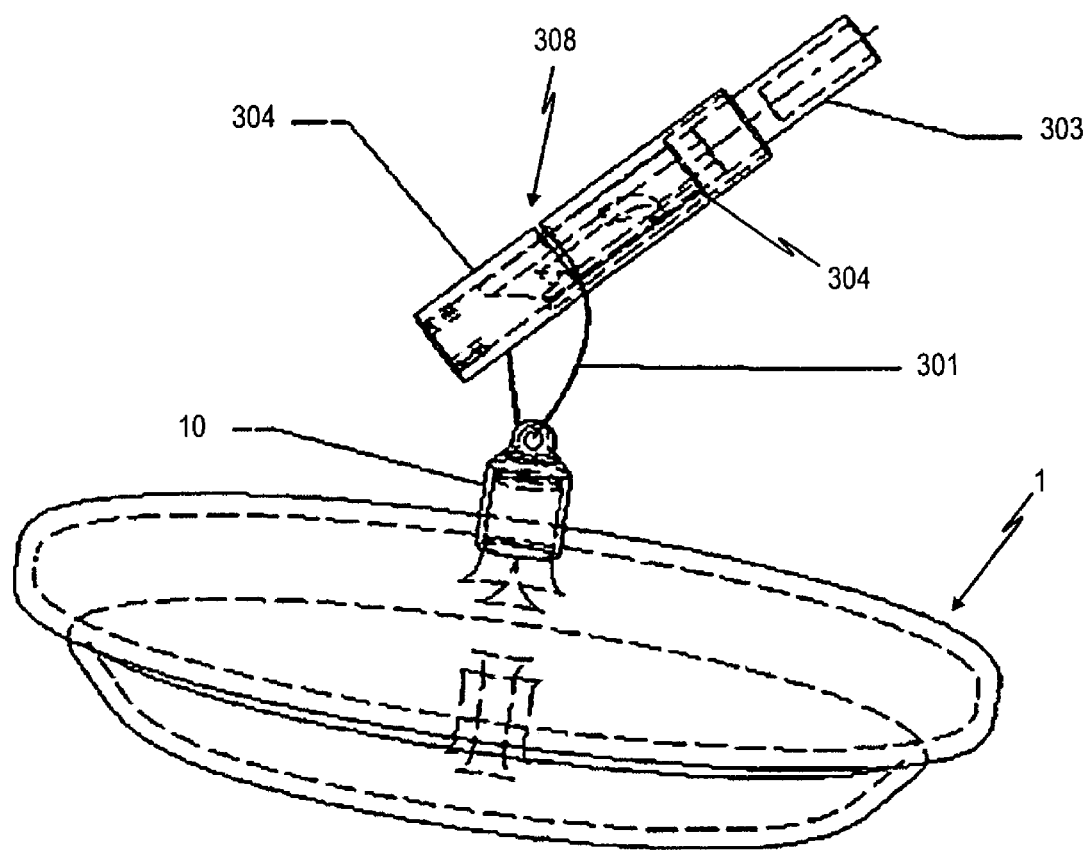
FIG. 24 shows an enlarged perspective representation of the forward section of the surgical instrument with an occlusion device in accordance with the third embodiment for depicting the coupling via a fastening loop.

FIG. 24 shows a representation similar to that of FIG. 23 whereby occlusion device 1 is also shown on holder 10, attached by means of holder 10 and by means of fastening loop 301 in cross-groove 308 of sleeve 304.

The following will more precisely describe the third embodiment method for the repeated coupling of an implant having a holder 10, in particular an occlusion device 1, to a surgical instrument 300:

In a first procedural step, a fastening loop 301 of defined length is fastened to eyelet 16 of the implant's holder 10. Fastening loop 301 is then inserted into cross-groove 308 of cylindrical sleeve 304 such that knot 311 of fastening loop 301 fits centrically through protrusion 309 and the section of fastening loop 301 positioning in cross-groove 308 is held diametrically. Upon a defined forward shifting of hook 302, the section of fastening loop 301 in cross-groove 308 namely slips over hook 302 in the second longitudinal groove 307 and remains anchored there. By withdrawing hook 302, holder 10 of the implant is pulled and clamped to the face side 305 of sleeve 304. A renewed defined forward displacing of hook 302 will again loosen fastening loop 301 and the proximal front side 305 of sleeve 304 will loosen from holder 10 and the seating of the implant can be checked. The use of fastening loop 301 allows recoupling of sleeve 304 to holder 10 of the implant at any time. An unintentional releasing of occlusion device 1 from surgical instrument 300 is prevented by the following measures: firstly, fastening loop 301 cannot slip off hook 302 by itself in the tensioned state. Secondly, neither can fastening loop 301 slip from hook 302 in the relaxed state since the hook opening is closed by the sleeve 304 which surrounds it. Thirdly, hook 302 is secured against twisting within the second longitudinal groove 307 of sleeve 304 so that neither can the hook opening position in front of cross-groove 308. Fourthly, blade 310 remains in secured state behind cross-groove 308 in second gripping section 110 due to stops 312, 313 and can thus neither contact nor sever the unrelaxed or tensioned fastening loop 301. Finally, blade 310 can only be led into gap 315 of hook 302 by conscious and deliberate interaction with the actuator member of the surgical instrument 300 and by its slight withdrawing from the tensioned fastening loop 301 in order to cut same. Only the slight retraction of surgical instrument 300 will diametrically tension fastening loop 301 through cross-groove 308 and only a defined forward displacement of hook 302 with its blade 310 can cut through fastening loop 301.

Since certain changes may be made in the above device without departure from the scope of the invention herein involved, it is intended that all matter contained in the above description, as shown in the accompanying drawings, the specification, and the claims shall be interpreted in an illustrative, and not limiting sense.

What is claimed is:

1. An occlusion device comprising:
a braiding of one of thin wires or threads which tapers to a diameter of a catheter used for an intravascular implantation or explantation procedure, said braiding, including:
a proximal retention area;
a distal retention area;
a cylindrical crosspiece interposed between said proximal retention area and said distal retention area; and
a holder disposed at said distal retention area, said holder having a first end portion in which ends of said wires or threads converge and a second end portion forming a substantially spherical surface having a cross-hole therethrough and a plurality of chamfered surfaces connecting said cross-hole with said substantially spherical surface, said chamfered surfaces offset towards an end of said second end portion.

\* \* \* \* \*